United States Patent [19]

Takaya et al.

[11] 4,254,117
[45] Mar. 3, 1981

[54] 7-(α,α-DISUBSTITUTED-ACETAMIDO)-3-SUBSTITUTED-3-CEPHEM-4-CARBOXYLIC ACIDS

[75] Inventors: Takao Takaya, Sakai; Takashi Masugi, Kitamachi; Hisashi Takasugi, Kohamanishi; Hiromu Kochi, Sakai, all of Japan

[73] Assignee: Fujisawa Pharmaceutical Co., Ltd., Osaka, Japan

[21] Appl. No.: 971,220

[22] Filed: Dec. 20, 1978

Related U.S. Application Data

[62] Division of Ser. No. 654,804, Feb. 3, 1976, Pat. No. 4,143,166.

[30] Foreign Application Priority Data

| Mar. 27, 1975 | [JP] | Japan | 50-37647 |
| Apr. 2, 1975 | [JP] | Japan | 50-15191 |
| Apr. 21, 1975 | [JP] | Japan | 50-48833 |
| Jun. 23, 1975 | [JP] | Japan | 50-78294 |
| Jul. 7, 1975 | [JP] | Japan | 50-83867 |

[51] Int. Cl.$^3$ ................. A61K 31/545; C07D 501/44
[52] U.S. Cl. ........................................ 424/246; 544/16
[58] Field of Search ................. 544/22, 16; 424/246

[56] References Cited

U.S. PATENT DOCUMENTS

| 3,962,227 | 6/1976 | Chauvette | 544/22 |
| 4,024,134 | 5/1977 | Gregson et al. | 544/22 |
| 4,033,950 | 7/1977 | Cook et al. | 544/22 |
| 4,122,259 | 10/1978 | Humber | 544/22 |

Primary Examiner—Paul M. Coughlan, Jr.
Attorney, Agent, or Firm—Dayton R. Stemple, Jr.

[57] ABSTRACT 7-(2-Hydroxyimino-2-hydroxyphenyl-acetamido)-3-substituted-3-cephem-4-carboxylic acids are disclosed which possess an antibacterial activity.

9 Claims, No Drawings

7-(α,α-DISUBSTITUTED-ACETAMIDO)-3-SUBSTITUTED-3-CEPHEM-4-CARBOXYLIC ACIDS

This is a division of application Ser. No. 654,804, filed Feb. 3, 1976, U.S. Pat. No. 4,143,166.

The present invention relates to a new 7-(α,α-disubstituted-acetamido)-3-substituted-3-cephem-4-carboxylic acid, its derivatives at the carboxy group and pharmaceutically acceptable salts thereof which possess an antibacterial activity and processes for the preparation thereof.

The new 7-(α,α-disubstituted-acetamido)-3-substituted-3-cephem-4-carboxylic acid of the present invention is represented by the following formula:

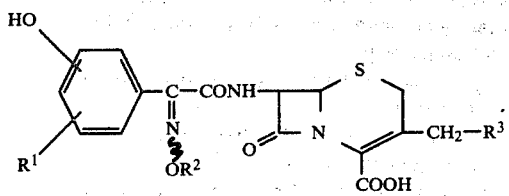

wherein
$R^1$ is hydrogen, halogen, hydroxy, nitro, lower alkoxy or acylamino,
$R^2$ is hydrogen or acyl and
$R^3$ is lower alkanoyloxy, carbamoyloxy which may have lower alkyl, aryl or protective group for amino, or a heterocyclicthio which may have lower alkyl.

With regard to the desired compound of this invention, it is to be understood that the compound of the formula (I) includes syn isomer, anti isomer and a mixture thereof.

In this specification, it is to be understood that the term "lower" used in connection with the moieties derived from alkane, alkene or alkyne is intended to mean a group having 1 to 6 carbon atom(s) unless otherwise indicated.

Further in this specification, syn isomer means one geometrical isomer having the group represented by the following formula:

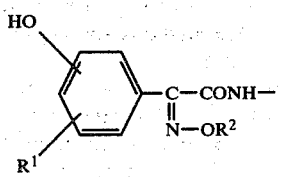

and anti isomer means the other geometrical isomer having the group of the formula:

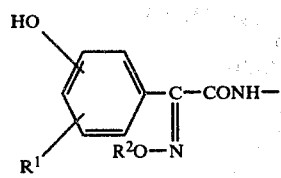

A suitable example of halogen may include chlorine, bromine, fluorine and iodine.

A suitable example of lower alkoxy may include one having 1 to 6 carbon atom(s) which may be branched, for example, methoxy, ethoxy, propoxy, isopropoxy, butoxy, isobutoxy, tertbutoxy, pentyloxy or hexyloxy, and preferably one having 1 to 4 carbon atom(s), and more preferably one having 1 to 2 carbon atom(s).

A suitable example of acylamino may include amino group having acyl as mentioned below, and preferably lower alkanesulfonamido having 1 to 6 carbon atom(s) such as mesylamino, ethanesulfonamido, propanesulfonamido, butanesulfonamido or hexanesulfonamido, and more preferably one having 1 to 4 carbon atom(s), and the most preferably one having 1 to 2 carbon atom(s).

A suitable example of acyl may include
lower alkanoyl having 1 to 6 carbon atom(s) (e.g., formyl, acetyl, propionyl, butyryl, isobutyryl, valeryl, pivaloyl, hexanoyl, etc.), and preferably one having 2 to 5 carbon atoms;
cyclo(lower)alkanecarbonyl (e.g., cyclopropanecarbonyl, cyclobutanecarbonyl, cyclopentanecarbonyl, cyclohexanecarbonyl, etc.); lower alkenoyl (e.g., acryloyl, crotonoyl, etc.);
aroyl having 7 to 11 carbon atoms, (e.g., benzoyl, toluoyl, xyloyl, naphthoyl, 4-isopropylbenzoyl, etc.), and preferably one having 7 to 8 carbon atoms;
lower alkoxycarbonyl having 2 to 7 carbon atoms (e.g., methoxycarbonyl, ethoxycarbonyl, propoxycarbonyl, isopropoxycarbonyl, butoxycarbonyl, isobutoxycarbonyl, 1,1-dimethylpropoxycarbonyl, tert-butoxycarbonyl, pentyloxycarbonyl, hexyloxycarbonyl, etc.), and preferably one having 3 to 5 carbon atoms;
aryloxycarbonyl (e.g., phenoxycarbonyl, tolyloxycarbonyl, xylyloxycarbonyl, etc.);
lower alkanesulfonyl (e.g., mesyl, ethanesulfonyl, propanesulfonyl, butanesulfonyl, hexanesulfonyl, etc.);
arenesulfonyl (e.g., benzenesulfonyl, tosyl, etc.);
heterocyclicoxycarbonyl (e.g., 8-quinolyloxycarbonyl, pyridyloxycarbonyl, etc.);
heterocycliccarbonyl (e.g., thenoyl, furoyl, nicotinoyl, isonicotinoyl, etc.);
carbamoyl; arylcarbamoyl (e.g., phenylcarbamoyl, tolylcarbamoyl, etc.);
lower alkylcarbamoyl (e.g., methylcarbamoyl, ethylcarbamoyl, etc.); lower alkylthiocarbamoyl (e.g., methylthiocarbamoyl, ethylthiocarbamoyl, etc.);
and arylthiocarbamoyl (e.g., phenylthiocarbamoyl, tolythiocarbamoyl, etc.).

The above-mentioned acyl groups may have at their optional position at least one substituent(s) such as aryl (e.g., phenyl, tolyl, etc.), aforesaid aroyl, halogen, cyano, cyclo(lower)alkyl (e.g., cyclopropyl, cyclopentyl, cyclohexyl, etc.), aforementioned lower alkoxy, lower alkylthio (e.g., methylthio, ethylthio, propylthio, isopropylthio, butylthio, pentylthio, hexylthio, etc.), aforesaid lower alkoxycarbonyl, amino, hydroxy, lower alkanoyloxy (e.g. acetoxy, propionyloxy, etc.), aryloxy (e.g., phenoxy, tolyloxy, xylyloxy, etc.), arylthio (e.g., phenylthio, tolylthio, xylylthio, etc.), heterocyclic group (e.g., thienyl, thiadiazolyl, tetrazolyl, pyridyl, oxadiazolyl, benzothiazolon-3-yl, etc.), heterocyclicoxy (e.g., pyridyloxy, etc.), heterocyclicthio (e.g., thiadiazolylthio, etc.), lower alkyl (e.g., methyl, ethyl, propyl, isopropyl, butyl, pentyl, hexyl, etc.), nitro, phenylazo, aforementioned lower alkanesulfonyl, lower alkanesulfonamido or lower alkanoylamino (e.g., acetamido, propionamido, etc.).

In the case that the acyl groups have more that two substituents, the substituents may be same or different.

In the aforesaid substituents aryl, aryloxy, arylthio and heterocyclic group may further have at their optical positions one or more aforesaid substituent(s) such as lower alkoxy, halogen, lower alkyl or nitro.

A preferable example of acyl having aforesaid substituent(s) may include mono(or di or tri)halo(lower)alkanoyl having 1 to 6 carbon atom(s) (e.g., chloroacetyl, chloropionyl, chlorobutyryl, dichloroacetyl, difluoroacetyl, dichlorohexanoyl, trifluoroacetyl, trichloroacetyl, etc.) or lower alkanoyl substituted with a sulfur atom containing unsaturated 5-membered heteromonocyclic group, for example, lower alkanoyl substituted with thienyl (e.g., thienylacetyl, thienylpropionyl, thienylhexanoyl, etc.), and in this case lower alkanoyl may be preferably one having 1 to 3 carbon atom(s).

A suitable example of lower alkanoyloxy may include one having 1 to 6 carbon atom(s) such as formyloxy, acetoxy, propionyloxy, butyryloxy, isobutyryloxy, valeryloxy, pivaloyloxy or hexanoyloxy, and preferably one having 1 to 4 carbon atom(s), and more preferably one having 1 to 2 carbon atom(s).

A suitable example of carbamoyloxy having lower alkyl may include lower alkylcarbamoyloxy having 2 to 7 carbon atoms such as methylcarbamoyloxy, ethylcarbamoyloxy, propylcarbamoyloxy or hexylcarbamoyloxy, and preferably one having 2 to 4 carbon atoms.

A suitable example of carbamoyloxy having aryl may include arylcarbamoyloxy having 7 to 8 carbon atoms such as phenylcarbamoyloxy or tolylcarbamoyloxy.

A suitable example of protective group for amino on the carbamoyloxy may include acyl such as halo(lower)alkanoyl having 2 to 3 carbon atoms (e.g., chloroacetyl, dichloroacetyl, trichloroacetyl, trifluoroacetyl etc.) or the like.

Suitable heterocyclicthio may include a saturated or unsaturated, monocyclic or polycyclic heterocyclicthio group which contains at least one hetero atom selected from oxygen, sulfur, nitrogen or the like.

A suitable example of the heterocyclicthio may be one having a heterocyclic group, such as
an unsaturated 5-membered heteromonocyclic containing a sulfur atom and 1 to 3 nitrogen atom(s), for example, thiazolyl, isothiazolyl, thiadiazolyl (e.g., 1,2,4-thiadiazolyl, 1,3,4-thiadiazolyl, 1,2,5-thiadiazolyl etc.), etc.,
an unsaturated 5-membered heteromonocyclic containing an oxygen atom and 1 to 3 nitrogen atom(s), for example, oxazolyl, isoxazolyl, oxadiazolyl (e.g., 1,2,4-oxadiazolyl, 1,3,4-oxadiazolyl, 1,2,5-oxadiazolyl etc.), etc.;
an unsaturated 5-membered heteromonocyclic containing 2 to 4 nitrogen atoms, for example, imidazolyl, pyrazolyl, triazolyl (e.g., 4H-1,2,4-triazolyl, 1H-1,2,3-triazolyl, 2H-1,2,3-triazolyl etc.), tetrazolyl (e.g., 1H-tetrazolyl, 2H-tetrazolyl etc.), etc.; an unsaturated benzene-fused heterocyclic containing nitrogen, sulfur and/or oxygen atom(s), for example, benzothiazolyl, benzimidazolyl or benzoxazolyl;
or a residue of an unsaturated 6-membered heteromonocyclic N-oxide containing 1 to 3 nitrogen atom(s) (e.g., pyridine-1-oxide, etc.).

And these heterocyclic groups may be optionally substituted with lower alkyl having 1 to 6 carbon atom(s) (e.g., methyl, ethyl, propyl, isopropyl, butyl, isobutyl, tert-butyl, pentyl, hexyl etc.), and preferably one having 1 to 4 carbon atom(s), and more preferably one having 1 to 2 carbon atom(s).

A suitable example of derivative at the carboxy group may include a conventional ester, for example,
lower alkyl ester (e.g., methyl ester, ethyl ester, propyl ester, isopropyl ester, butyl ester, isobutyl ester, tert-butyl ester, tert-pentyl ester etc.);
lower alkanesulfonyl(lower)alkyl ester (e.g., 2-mesylethyl ester, 3-mesylpropyl ester etc.);
halo(lower)alkyl ester (e.g. trichloromethyl ester, 2-iodoethyl ester, 2,2,2-trichloroethyl ester etc.);
ar(lower)alkyl ester which may have lower alkoxy, nitro or hydroxy [e.g., benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-di-tert-butylbenzyl ester etc.];
aroyl(lower)alkyl ester (e.g., phenacyl ester, toluoylmethyl ester etc.);
lower alkoxy(lower)alkyl ester (e.g., methoxymethyl ester, ethoxymethyl ester etc.);
lower alkanoyl(lower)alkyl ester (e.g., acetonyl ester, propionylmethyl ester etc.);
cyclo(lower)alkyl(lower)alkyl ester (e.g., 1-cyclopropylethyl ester, 2-cyclopropylpropyl ester etc.);
lower alkenyl ester (e.g., allyl ester, isopropenyl ester etc.);
lower alkynyl ester (e.g., ethynyl ester, propynyl ester etc.); or lower alkanoyloxy(lower)alkyl ester having 2 to 12 carbon atoms (e.g., acetoxymethyl ester, propionyloxymethyl ester, butyryloxyethyl ester, pivaloyloxymethyl ester, hexanoyloxyhexyl ester etc.), and preferably one having 2 to 7 carbon atoms.

A suitable example of pharmaceutically acceptable salts may be inorganic salt such as an alkali metal salt (e.g., sodium salt or potassium salt), an alkaline earth metal salt (e.g., calcium salt or magnesium salt) or a salt with an organic base such as trimethylamine, triethylamine, dicyclohexylamine, arginine or the like.

All or some of the object compound (I), its derivatives at the carboxy group and pharmaceutically acceptable salts thereof of the present invention may be prepared by various methods and typical ones of them are illustrated as follows:

(A): One typical method for the preparation of the object compound (I), its derivatives at the carboxy group and pharmaceutically acceptable salts thereof is represented by the following scheme:

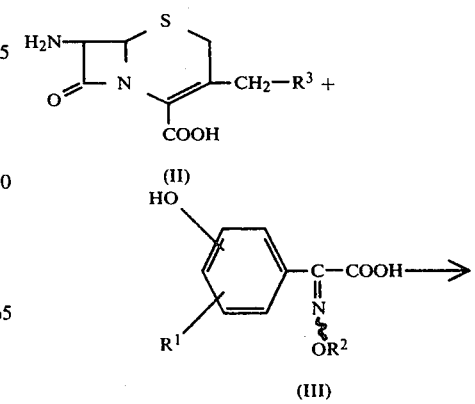

-continued

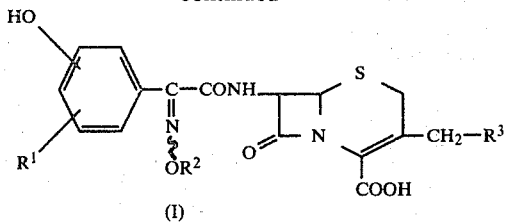

wherein $R^1$, $R^2$ and $R^3$ are each as defined above.

The present reaction is carried out by reacting 7-amino-3-substituted-3-cephem-4-carboxylic acid (II) or its derivatives at the amino and/or carboxy group or salts thereof with α,α-disubsituted acetic acid (III) or its reactive derivatives at the carboxy group or salts thereof, and if necessary, subjecting the resulting compound wherein $R^2$ is acyl to elimination reaction of the acyl group.

Among α,α-disubstituted acetic acid (III) used as a starting compound in the present reaction, for example, 2-hydroxyimino-2-(3-mesylamino-4-hydroxyphenyl)acetic acid (syn isomer) can be prepared by reducing 3-nitro-4-benzyloxyacetophenone, reacting the resulting 3-amino-4-benzyloxyacetophenone with mesyl chloride, oxidizing the resulting 3-mesylamino-4-benzyloxyaceto phenone, reacting the resulting 3-mesylamino-4-benzyloxyphenylglyoxylic acid with acid and reacting the resulting 3-mesylamino-4-hydroxyphenylglyoxylic acid with hydroxylamine; and 2-pivaloyloxyimino-2-(3-hydroxyphenyl)acetic acid (syn isomer) can be prepared by reacting 3-hydroxyphenylglyoxylic acid with hydroxylamine and then reacting the resulting 2-hydroxyimino-2-(3-hydroxyphenyl)acetic acid (syn isomer) with pivaloyl chloride;
and
other compounds (III) can be prepared according to similar manners as mentioned above. in this preparation of the starting compound, in case that a substituted glyoxylic acid is reacted with hydroxylamine, syn isomer, anti isomer or a mixture thereof can be obtained according to reaction condition or the like.

A suitable derivative at the amino group of the compound (II) may include isocyanato, isothiocyanato, or Schiff's base or its tautomeric enamine type isomer formed by the reaction of the amino group with an aldehyde compound (e.g., acetaldehyde, isopentaldehyde, benzaldehyde, salicylaldehyde, phenylacetaldehyde, p-nitrobenzaldehyde, m-chlorobenzaldehyde, p-chlorobenzaldehyde, hydroxynaphthoaldehyde, furfural, thiophenecarboaldehyde etc.) or a ketone compound (e.g., acetone, methyl ethyl ketone, methyl isobutyl ketone, acetylacetone, ethyl acetoacetate etc.), or the like.

A suitable derivative at the carboxy group of the compound (II) can also be referred to the ones exemplified for the compound (I).

The salts of the compound (II) may be salts at the carboxy group, for example, a salt with an inorganic base such as an alkali metal salt (e.g., sodium or potassium salt) or an alkaline earth metal salt (e.g., calcium or magnesium salt), a salt with an organic base such as trimethylamine, triethylamine, dicyclohexylamine or the like, and salts at the amino group, for example, salts with an acid such as a salt with an inorganic acid (e.g., hydrochloric acid or sulfuric acid), a salt with an organic acid (e.g., acetic acid, tartaric acid, maleic acid, benzenesulfonic acid or toluenesulfonic acid).

The compound of the formula (III) may be syn isomer, anti isomer or a mixture thereof.

The salts of the compound (III) may be salts with an inorganic base such as an alkali metal salts (e.g., sodium or potassium salt) or an alkaline earth metal salt (e.g., calcium or magnesium salt), a salt with an organic base such as trimethylamine, triethylamine, dicyclohexylamine or the like.

The suitable reactive derivatives at the carboxy group of the compound (III) may include, for example, an acid halide, an acid anhydride, an activated amide, an activated ester, and preferably an acid chloride; an acid azide;
a mixed acid anhydride with an acid such as dialkylphosphoric acid, phenylphosphoric acid, diphenylphosphoric acid, dibenzylphosphoric acid, halogenated phosphoric acid, dialkylphosphorous acid, sulfurous acid, thiosulfuric acid, sulfuric acid, alkylcarbonic acid, aliphatic carboxylic acid (e.g., pivalic acid, pentanoic acid, isopentanoic acid, 2-ethylbutyric acid, trichloroacetic acid etc.), aromatic carboxylic acid (e.g., benzoic acid etc.), or a symmetrical acid anhydride;
an acid amide with imidazole, 4-substituted imidazole, dimethylpyrazole, triazole or tetrazole; or
an ester (e.g., cyanomethyl ester, methoxymethyl ester, vinyl ester, propargyl ester, p-nitrophenyl ester, 2,4-dinitrophenyl ester, trichlorophenyl ester, pentachlorophenyl ester, methanesulfonylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or an ester with N,N-dimethylhydroxylamine, 1-hydroxy-2-(1H)-pyridone, N-hydroxysuccinimide, N-hydroxyphthalimide 1-hydroxybenzotriazole, 1-hydroxy-6-chlorobenzotriazole etc.), or the like. The suitable reactive derivative can be optionally selected from them according to the kind of the α,α-disubstituted acetic acid (III) to be used practically.

In the present reaction, the compound (II) may be reacted in advance with a silyl compound [e.g., chlorotrimethylsilane or bis(trimethylsilyl)acetamide] to give a silyl derivative of the compound (II) at the carboxy group or the amino and carboxy groups, which is subjected to the reaction with the compound (III) or its reactive derivatives at the carboxy group or salts thereof, and this is also included in the scope of the present reaction.

The reaction is usually carried out in a solvent such as water, acetone, dioxane, acetonitrile, chloroform, methylene chloride, ethylene chloride, tetrahydrofuran, ethyl acetate, dimethylformamide, pyridine or any other organic solvent which does not adversely affect the reaction. Among these solvents, hydrophilic solvents may be used in a mixture with water.

When the α,α-disubstituted acetic acid (III) is used in a form of the free acid or salt in this reaction, the reaction is preferably carried out in the presence of a condensing agent such as N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N'-carbonyldi(2-methylimidazole), pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, N-ethyl-benzisoxazolium salt, N-ethyl-5-phenyl-isoxazolium-3'-sulfonate, Vilsmeier reagent such as (chloromethylene)dimethylammonium chloride or the like, or the like.

Also, the reaction may be carried out in the presence of a base, for example, an inorganic base such as alkali metal hydroxide, alkali metal bicarbonate, or alkali metal carbonate; or an organic base such as trialkylamine, N,N-dialkylbenzylamine, alkali metal alkoxide, N,N-dialkylaniline or pyridine. When the base or the condensing agent is in liquid, it can be used also as a solvent. The reaction temperature is not critical, and the reaction is usually carried out under cooling or at ambient temperature.

In the present acylating reaction, when the compound (III) wherein $R^2$ is acyl group is used as the starting compound, there may be obtained occasionally either the object compound (I) wherein $R^2$ is acyl group or hydrogen according to a kind of the acyl group for $R^2$, reaction conditions etc., and when the compound (II) wherein $R^3$ is carbamoyloxy group having protective group for amino is used as the starting compound, there may be obtained occasionally either the object compound (I) wherein $R^3$ is carbamoyloxy group having protective group for amino or carbamoyloxy group according to reaction conditions. And, in case that the compound (I) wherein $R^2$ is acyl group is obtained in the present acylating reaction, if necessary, it may be further subjected to elimination reaction of the acyl group for $R^2$ to provide the compound (I) wherein $R^2$ is hydrogen. And in this elimination reaction of the acyl group for $R^2$, carbamoyloxy having protective group for amino may be changed to free carbamoyloxy.

The elimination reaction of the acyl group may include an elimination method using a base, for example, an inorganic base such as an alkali metal hydroxide (e.g., sodium hydroxide, potassium hydroxide etc.), an alkali metal bicarbonate (e.g., sodium bicarbonate, potassium bicarbonate etc.) or an alkali metal carbonate (e.g., sodium carbonate, potassium carbonate etc.), an organic base such as an alkali metal alkoxide (e.g., sodium methoxide, sodium ethoxide etc.), a trialkylamine (e.g., trimethylamine, triethylamino etc.), triethanolamine, N,N-dimethylaniline, N,N-dimethylbenzylamine, N-methylmorpholine or pyridine; and an elimination reaction using silica gel, basic or acidic alumina, basic or acidic ion exchange resin, thiourea, trifluoroacetic acid, trifluoroacetic acid.anisole, copper.dimethylformamide, zinc.dimethylformamide, zinc.acetic acid, zinc.formic acid, trifluoroacetic acid.zinc etc. The present elimination reaction is usually carried out in water, hydrophilic solvent or a mixture thereof. The reaction temperature is not critical and the reaction is preferably carried out at ambient temperature or under cooling.

In the reaction of the compound (II) with the compound (III) or the elimination reaction of the acyl group, syn or anti isomer of the compound (III) may be partially or wholly isomerized according to reaction conditions, a kind of acyl group etc., and the derivatives at the carboxy group or salts in the compound (II) may be converted into their free form in the course of the reaction or in post-treatment.

The starting compounds (II), (III) and the object compound (I), its derivatives at the carboxy group and pharmaceutically acceptable salt thereof being all comparatively unstable compounds and easily decomposed in the course of the reaction, it is desirable to conduct the reaction and the isolation procedure of the product under a mild condition.

(B): Another typical method for the preparation of some of the object compound (I), its derivatives at the carboxy group or pharmaceutically acceptable salts thereof is represented by the following scheme:

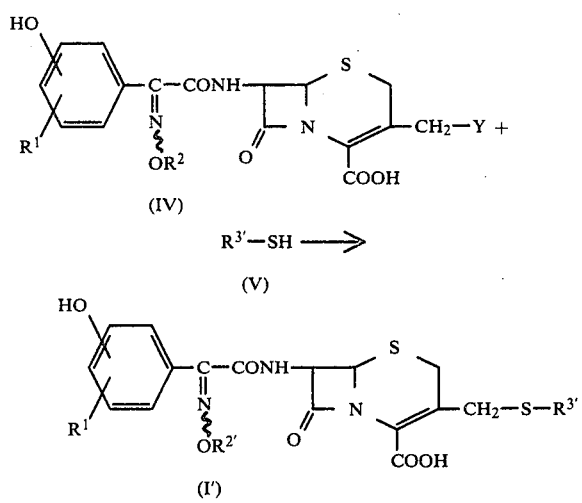

in which Y is a group which can be substituted by a group $R^{3'}-S-$ wherein $R^{3'}$ is a heterocyclic group which may have lower alkyl, $R^{2'}$ is hydrogen, lower alkanoyl, cyclo(lower)alkanecarbonyl or aroyl and $R^1$, $R^2$ and $R^{3'}$ are each as defined above.

The present reaction is carried out by reacting the compound (IV) or its derivatives at the carboxy group or salts thereof with a thiol compound (V) or salts thereof, and if necessary, subjecting the resulting compound to elimination reaction of acyl group.

The compound of the formula (IV) may be syn isomer, anti isomer or a mixture thereof.

A suitable example of a group which can be substituted by a group $R^{3'}-S-$ may include halogen, azido and acyloxy wherein said halogen and acyl moiety of said acyloxy are the same ones as aforementioned.

A suitable example of a heterocyclic group, lower alkyl, lower alkanoyl, cyclo(lower)alkanecarbonyl or aroyl can also be referred to the ones exemplified for the compound (I) respectively.

A suitable derivative at the carboxy group of the compound (IV) can also be referred to the ones exemplified for the compound (I) and the salts of the compound (IV) can be referred to the ones exemplified for the compound (III).

The suitable example of salts of the compound (V) may be alkali metal salts (e.g., sodium salt, potassium salt etc.).

The present reaction may be carried out in a solvent such as water, acetone, chloroform, nitrobenzene, methylene chloride, ethylene chloride, dimethylformamide, methanol, ethanol, ether, tetrahydrofuran, dimethylsulfoxide, or any other organic solvent which does not adversely affect the reaction, preferably in ones having strong polarities. Among the solvents, hydrophilic solvents may be used in a mixture with water. The reaction is preferably carried out in around neutral medium. When the compound (IV) or the thiol compound (V) is used in a free form, the reaction is preferably conducted in the presence of a base, for example, inorganic base such as alkali metal hydroxide, alkali metal carbonate, alkali metal bicarbonate, organic base such as trialkylamine, and the like. The reaction temperature is not critical, and the reaction is usually carried out at ambient temperature or under warming. The reaction product can be isolated from the reaction mixture by conventional methods.

In the present reaction, when the compound (IV) having an acyl group as $R^2$ is used as the starting compound, the object compound (I') having a hydrogen atom as $R^{2'}$ may be directly obtained according to a kind of the acyl group for $R^2$, reaction conditions etc. When the resulting compound having an acyl group on hydroxyimino group is obtained in the present reaction, it may be subjected to elimination reaction of the acyl group, if necessary.

The elimination reaction of the acyl group can be carried out according to similar manners as mentioned above.

In the reaction of the compound (IV) with the compound (V) or the elimination reaction of the acyl group, syn or anti isomer of the compound (IV) may be partially or wholly isomerized according to reaction conditions, a kind of acyl group etc. and the derivatives at the carboxy group or salts in the compound (IV) may be converted into their free form in the course of the reaction or in post-treatment.

The starting compounds (IV) and the object compound (I'), its derivatives at the carboxy group and pharmaceutically acceptable salts thereof being all comparatively unstable compounds and easily decomposed in the course of the reaction, it is desired to conduct the reaction and the isolation procedure of the product under a mild condition.

The starting compound (IV) is novel and can be prepared according to other methods disclosed in this specification.

(C): Further alternative method of the preparation of some of the object compound (I), its derivatives at the carboxy group or pharmaceutically acceptable salts thereof is represented by the following scheme:

A suitable example of acyl for $R^{2''}$ can also be referred to the ones exemplified for the compound (I).

A suitable example of derivative at the carboxy group of the compound (I'') can also be referred to the ones exemplified for the compound (I), and the salts of the compound (I'') can be referred to the ones exemplified for the compound (III).

The compound of the formula (I'') may be syn isomer, anti isomer or a mixture thereof.

The acylating agent to be used for the present reaction may include an aliphatic, aromatic and heterocyclic carboxylic acid, and the corresponding sulfonic acid and thio acid which have aforesaid acyl group as their acyl moieties, and reactive derivatives of the above-mentioned acids. A suitable reactive derivative of the acids can be referred to the ones exemplified for the compound (III).

The acylating agent may further include isocyanic acid ester (e.g., methyl isocyanate, phenyl isocyanate etc.), isothiocyanic acid ester (e.g., methyl isothiocyanate, phenyl isothiocyanate etc.) and haloformic acid ester (e.g., ethyl chloroformate, benzyl chloroformate etc.). In this case, for example, when methyl isocyanate is used as an acylating agent, methylcarbamoyl group is introduced as acyl group of $R^{2''}$ and when ethyl chloroformate is used as an acylating agent, ethoxycarbonyl group is introduced as acyl group of $R^{2''}$.

In the present reaction, the compound (I'') may be reacted in advance with a silyl compound [e.g., chlorotrimethylsilane, bis(trimethylsilyl)acetamide etc.] to give a silyl derivative at the hydroxyimino group or the hydroxyimino and carboxy groups of the compound (I''), and then which may be reacted with the acylating agent.

The present reaction is carried out according to similar reaction conditions to those of aforesaid reaction of the compound (II) with the compound (III).

In the reaction of the compound (I'') with an acylating agent, syn or anti isomer of the compound (I'') may be partially or wholly isomerized according to reaction conditions, a kind of acyl group etc. and the derivatives at the carboxy group or salts in the compound (I'') may be converted into their free form in the course of

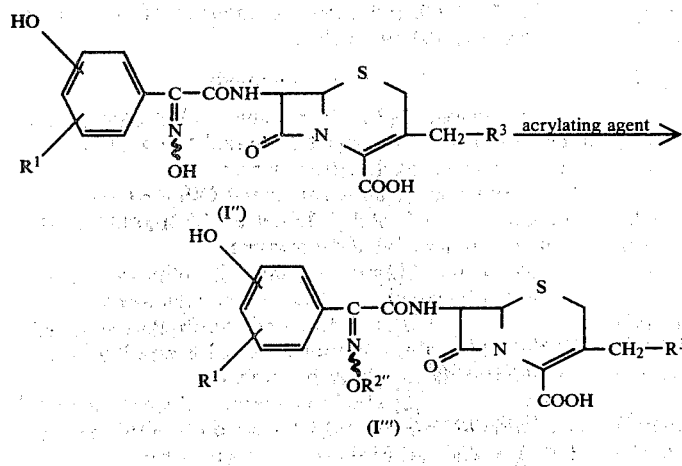

wherein $R^1$ and $R^3$ are each as defined above, and $R^{2''}$ is acyl.

The present reaction is carried out by reacting the compound (I''), its derivatives at the carboxy group or salts thereof with an acylating agent.

the reaction or in post-treatment.

The starting compounds (I'') and the object compound (I'''), its derivatives at the carboxy group and pharmaceutically acceptable salts thereof being all comparatively unstable compounds and easily decomposed in the course of the reaction, it is desired to conduct the reaction and the isolation procedure of the product under a mild condition.

The starting compound (I″) is novel and can be prepared by other methods disclosed in this specification.

(D): Further one alternative method of the preparation of the object compound wherein derivative at the carboxy group is ester, is represented by the following scheme:

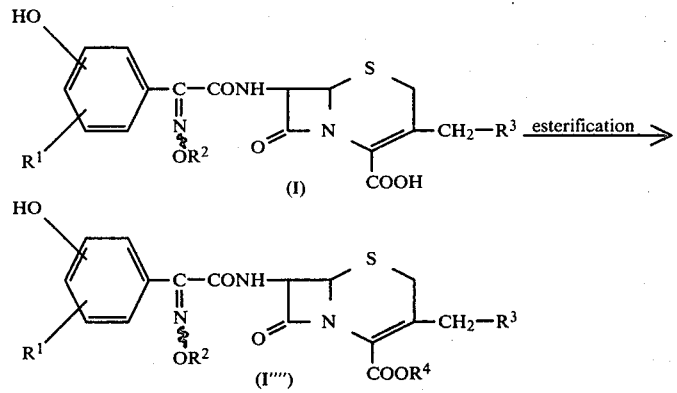

wherein $R^1$, $R^2$ and $R^3$ are each as defined above and $R^4$ is an ester moiety of an esterified carboxy represented by the formula:—$COOR^4$.

The present reaction is carried out by subjecting the compound (I) or salts thereof to esterification.

A suitable salt of the compound (I) can be also referred to the ones exemplified for the compound (III).

A suitable example of $R^4$ may include ester moiety of the ester exemplified for the derivative at the carboxy group of the compound (I).

The esterifying agent to be used in the present reaction may be a compound of the formula:

$$X—R^4 \qquad (VI)$$

wherein $R^4$ is as defined above and X is hydroxy or reactive derivatives thereof.

A suitable example of reactive derivative of hydroxy may include aforesaid halogen and the like.

The present reaction is usually carried out in a solvent such as dimethylformamide, pyridine, hexamethyl-phosphoric triamide or other solvents which does not adversely affect the reaction.

In case that the compound (I) is used in a form of free acid, the reaction is preferably carried out in the presence of a base, for example, an inorganic base such as aforesaid alkali metal hydroxide, alkali metal bicarbonate or alkali metal carbonate, or an organic base such as trialkylamine, N,N-dialkylaniline, N,N-dialkylbenzylamine or pyridine. The reaction temperature is not critical and the reaction is preferably carried out under cooling, at ambient temperature or under warming.

When thus obtained object compounds (I), (I′) and (I‴) are free acids, these compounds may be converted into pharmaceutically acceptable salts thereof by the conventional methods.

The object compounds of the present invention (I) exhibit high antibacterial activity and inhibit the growth of a number of microorganisms including Gram-positive and Gram-negative bacteria. For therapeutic administration, the cephalosporin compounds according to the present invention are used in the form of pharmaceutical preparation which contain said compounds in admixture with a pharmaceutically acceptable carriers such as an organic or inorganic solid or liquid excipient suitable for oral, parenteral or external administration. The parmaceutical preparations may be in solid form such as capsules, tablets, dragees, ointments or suppositories, or in liquid form such as solutions, suspensions, or emulsions. If desired, there may be included in the above preparations auxiliary substances, stabilizing agents, wetting or emulsifying agents, buffers and other commonly used additives.

While the dosage of the compounds will vary from and also depend upon the age and condition of the patient, an average single dose of about 50 mg., 100 mg., 250 mg., and 500 mg. of the compounds according to the present invention has proved to be effective in treating diseases caused by bacterial infection. In general amounts between 1 mg. and about 1000 mg. or even more may be administered.

The compounds closely related to the compounds of the present invention are disclosed in German Offenlegungsschrift 2204060.

Now for the purpose of showing that the object compounds (I) of the present invention have unexpectedly superior properties over the prior related compounds, the comparative test data on anti-microbial activity between a compound of the German Offenlegungsschrift 2204060 and some compounds of the present invention are shown below.

Test compounds (1) Sodium 7-[2-hydroxyimino-2-(4-hydroxyphenyl)acetamido]-3-(1-methyl-1H-tetrazol-5-yl)thiomethyl-3-cephem-4-carboxylate (syn isomer)

(2) Sodium 7-[2-hydroxyimino-2-(3-hydroxyphenyl)acetamido]-3-(1-methyl-1H-tetrazol-5-yl)thiomethyl-3-cephem-4-carboxylate (syn isomer)

(3) Sodium 7-[2-hydroxyimino-2-(3-chloro-4-hydroxyphenyl)acetamido]cephalosporanate (syn isomer)

(4) 7-[2-Hydroxyimino-2-(3-hydroxyphenyl)acetamido]-3-(1,3,4-thiadiazol-2-yl)thiomethyl-3-cephem-1-carboxylic acid (syn isomer)

(5) 7-[2-Hydroxyimino-2-(3-hydroxyphenyl)acetamido]-3-(5-methyl-1,3,4-thiadiazol-2-yl)thiomethyl-3-cephem-4-carboxylic acid (syn isomer)

(6) 7-[2-Benzoyloxyimino-2-(3-hydroxyphenyl)acetamido]-3-(1-methyl-1H-tetrazol-5-yl)thiomethyl-3-cephem-4-carboxylic acid (syn isomer)

(7) 7-[2-Ethoxycarbonyloxyimino-2-(3-hydroxyphenyl)acetamido]-3-(1-methyl-1H-tetrazol-5-yl)thiomethyl-3-cephem-4-carboxylic acid (syn isomer)

(8) 7-[2-Hydroxyimino-2-(3-hydroxyphenyl)acetamido]cephalosporanic acid (syn isomer)

(9) Sodium 7-[2-hydroxyimino-2-(3-hydroxyphenyl)acetamido]-3-carbamoyloxymethyl-3-cephem-4-carboxylate (syn isomer)

(10) 7-[2-Hydroxyimino-2-(3-nitro-4-hydroxyphenyl)acetamido]-3-(1-methyl-1H-tetrazol-5-yl)thiomethyl-3-cephem-4-carboxylic acid (syn isomer)

A compound disclosed in German Offenlegungsschrift (A) 7-(2-Hydroxyimino-2-phenylacetamido)-3-(5-methyl-1,3,4-thiadiazol-2-yl)thiomethyl-3-cephem-4-carboxylic acid (syn isomer)

Test Method

In vitro antibacterial activity was determined by the two-fold agar-plate dilution method as described below.

One loopful of an overnight culture of each test strain in Trypticase-soy broth ($10^8$ viable cells per ml) was streaked on heart infusion agar (HI-agar) containing graded concentrations of antibiotics, and the minimal inhibitory concentration (MIC) was expressed in terms of $\mu g/ml$ after incubation at 37° C. for 20 hours.

(Test results)

| Test Bacteria | | MIC ($\mu g/ml$) Test Compounds | | | | | | | | | | |
|---|---|---|---|---|---|---|---|---|---|---|---|---|
| | | (A) | (1) | (2) | (3) | (4) | (5) | (6) | (7) | (8) | (9) | (10) |
| Sh. flexneri | 2a | 6.25 | 1.78 | 0.78 | 3.13 | 0.39 | 0.39 | 0.78 | 1.56 | 0.78 | 0.78 | 1.56 |
| Sal. Enteritidis | | 6.25 | 3.13 | 1.56 | 0.78 | 0.39 | 0.2 | 0.39 | 0.2 | 1.56 | 0.78 | 0.2 |
| Ps. aeruginosa | 721 | 50 | 25 | 100 | 3.13 | 25 | 12.5 | 6.25 | 12.5 | 25 | 25 | 6.25 |
| E. coli | 341 | 12.5 | 1.56 | 0.78 | 6.25 | 0.78 | 0.78 | 1.56 | 3.13 | 0.78 | 1.56 | 3.13 |
| Kl. pneumoniae | 417 | 12.5 | 3.13 | 0.78 | 3.13 | 3.13 | 0.78 | 0.39 | 0.39 | 1.56 | 0.2 | 0.39 |
| Pr. mirabilis | 525 | 25 | 1.56 | 1.56 | 0.39 | 1.56 | 3.13 | 0.78 | 0.39 | 1.56 | 0.78 | 0.2 |

As clearly seen from the above test results, the compounds of the present invention (I) characterized in having hydroxy group on the benzene nucleus at 7 position in the molecule can be proved to show stronger antimicrobial activities against various pathogenic microorganisms as compared with that of the prior related compound.

The following examples are given for the purpose of illustrating the present invention.

PREPARATION OF THE STARTING COMPOUNDS

Preparation 1

(1) A mixture of 3-nitro-4-benzyloxyacetophenone (40 g.), 99% ethanol (800 ml.) and water (300 ml.) was warmed at 80° C. To the mixture was added sodium sulfide nonahydrate (80 g.) with stirring over 1 hour and then the mixture was refluxed with stirring for 3 hours. The reaction mixture was concentrated to the volume of 300 ml. at 40° C. under reduced pressure. Precipitating materials were collected by filtration, washed with water and dried to give 3-amino-4-benzyloxyacetophenone (25.5 g.), mp 115° to 114° C.

(2) A solution of mesyl chloride (6.3 g.) in dry methylene chloride (20 ml.) was dropwise added over 30 minutes with stirring and ice-cooling to a solution of 3-amino-4-benzyloxyacetophenone (12 g.) and dry pyridine (8.0 g.) in dry methylene chloride (100 ml.), and the mixture was stirred for 4 hours at ambient temperature. The reaction mixture was concentrated at 40° C. under reduced pressure and to the residue was added conc. hydrochloric acid to give pH 1 solution. Precipitates were collected by filtration, washed with water and dried to give 3-mesylamino-4-benzyloxyacetophenone (15.4 g.), mp 124° to 127° C.

(3) A mixture of 3-chloro-4-hydroxyacetophenone (11.9 g.), benzyl chloride (9.35 g.), potassium carbonate (14.5 g.) and dimethylformamide (60 ml.) was stirred for 1 hour at 100° C. The reaction mixture was poured into water (150 ml.) and extracted with ethyl acetate. The extract was washed with a sodium chloride aqueous solution and dried over magnesium sulfate. After distilling off the solvent, the residue (18 g.) was recrystallized from ethanol (160 ml.) to give 3-chloro-4-benzyloxyacetophenone (13.2 g.), mp 110° to 112° C.

Preparation 2

(1) Selenium dioxide powder (12.6 g.) was added over 10 minutes to a solution of 3-chloro-4-benzyloxyacetophenone (19.7 g.) in dry pyridine (100 ml.) with stirring at 100° C., and the mixture was stirred for 3 hours at the same temperature. Precipitating selenium was filtered of and the filtrate was concentrated. The residue was dissolved in water (150 ml.) and the solution was washed with ether. The aqueous solution was acidified under cooling with conc. hydrochloric acid and extracted with ether. The extract was washed with a sodium chloride aqueous solution, dried over magnesium sulfate and concentrated to give 3-chloro-4-benzyloxyphenylglyoxylic acid (15.9 g.), mp 134° to 135° C.

(2) The following compounds were obtained according to a similar manner to that of Preparation 2(1).

(1) 3-Nitro-4-benzoyloxyphenylglyoxylic acid, mp 161° to 164° C.

(2) 3-Mesylamino-4-benzyloxyphenylglyoxylic acid, mp 165° to 167° C. (dec.).

Preparation 3

(1) A mixture of 3-nitro-4-benzyloxyphenylglyoxylic acid (30 g.), conc. hydrochloric acid (90 ml.) and acetic acid (120 ml.) was stirred for 3 hours at 100° C. To the reaction mixture was added under cooling ice-water (600 ml.) and the mixture was extracted with ethyl acetate. The extract was washed with ice-water, dried over magnesium sulfate and concentrated to dryness under reduced pressure. The residue was recrystallized from a mixture of benzene: ether: petroleum ether (2:1:4). The crystals were collected by filtration, washed with benzene and dried under reduced pressure to give 3-nitro-4-hydroxyphenylglyoxylic acid (19.0 g.), mp 139° to 140.5° C.

(2) The following compounds were obtained according to a similar manner to that of Preparation 3(1).

(1) 3-Mesylamino-4-hydroxyphenylglyoxylic acid, mp 163° to 165° C.

(2) 3-Chloro-4-hydroxyphenylglyoxylic acid, mp 114° to 116° C.

Preparation 4

(1) To a solution of sodium bicarbonate (5.56 g.) in water (200 ml.) was added and dissolved with stirring 3-hydroxyphenylglyoxylic acid (11 g.) under cooling. On the other hand, hydroxylamine hydrochloride (4.60 g.) was added and dissolved into a solution of sodium bicarbonate (5.56 g.) in water (70 ml.) with stirring at room temperature. Thus obtained solution was added with stirring to the above obtained solution under cooling. The mixture was stirred for 20 hours at room temperature and was subjected for salting-out treatment. Then, the reaction solution was acidified with hydrochloric acid and was extracted with ethyl acetate. The extract was washed with saturated aqueous solution of sodium chloride and dried. After solvent was distilled off, the residue was crystallized from benzene. The crystals were collected by filtration to obtain 2-hydroxyimino-2-(3-hydroxyphenyl)acetic acid (syn isomer) (6 g.).

I.R. Spectrum (Nujol) 3200–3350, 1700 cm$^{-1}$ (2) A mixture of 3-hydroxyphenylglyoxylic acid (3.32 g.) and 1 N-methanol solution of hydroxylamine (45 ml.) was refluxed with stirring, for 25 minutes. The reaction mixture was concentrated to dryness. The residue was dissolved in 1 N-sodium hydroxide aqueous solution (50 ml.) and the solution was washed with ether, acidified with hydrochloric acid under cooling and extracted with ethyl acetate. The extract was washed with a saturated sodium chloride aqueous solution, dried and concentrated to give yellow oil. To the oil was added benzene and benzene was distilled off. The residue was crystallized with petroleum ether and the crystals were collected by filtration, washed with petroleum ether and dried to give 2-hydroxyimino-2-(3-hydroxyphenyl)acetic acid (a mixture of syn and anti isomer) (2.9 g.).

I.R. Spectrum (Nujol) 3200, 1700 cm$^{-1}$ (3) The following compounds were obtained according to a similar manner to that of Preparation 4(1).

(1) 2-Hydroxyimino-2-(3-methoxy-4-hydroxyphenyl)acetic acid (syn isomer).

I.R. Spectrum (Nujol) 3250–3350, 1710 cm$^{-1}$ (2) 2-Hydroxyimino-2-(3-nitro-4-hydroxyphenyl)acetic acid (syn isomer), mp 170° to 171.5° C. (dec.).

(3) 2-Hydroxyimino-2-(3-chloro-4-hydroxyphenyl)acetic acid (syn isomer), mp 162° C. (dec.).

(4) 2-Hydroxyimino-2-(3-mesylamino-4-hydroxyphenyl)acetic acid (syn isomer), mp 94° to 95° C. (dec.).

Preparation 5

(1) Dichloroacetyl chloride (8.14 g.) was dissolved in methylene chloride (25 ml.), and to this solution was added under cooling 2-hydroxyimino-2-(3-hydroxyphenyl)acetic acid (syn isomer) (2.5 g.) with stirring, and then the resultant mixture was stirred for 45 minutes at room temperature. Petroleum ether was added to the reaction mixture and the precipitates were collected by filtration, and then thoroughly washed with petroleum ether to give 2-dichloroacetoxyimino-2-(3-hydroxyphenyl)acetic acid (syn isomer) (3.57 g.).

I.R. Spectrum (Nujol) 3450, 1765, 1740 cm$^{-1}$ (2) A mixture of 2-hydroxyimino-2-(3-hydroxyphenyl)acetic acid (syn isomer) (9.06 g.), benzoyl chloride (32.25 g.) and tetrahydrofuran (50 ml.) was stirred for 6 hours at ambient temperature. To the reaction mixture was added petroleum ether under 5° C. Precipitates were collected by filtration, washed with petroleum ether and dried to give 2-benzoyloxyimino-2-(3-hydroxyphenyl)acetic acid (syn isomer) (11.12 g.), mp 140° to 142° C. (dec.).

(3) Dichloroacetyl chloride (14.7 g.) was dissolved in methylene chloride (50 ml.). To the solution was added 2-hydroxyimino-2-(3-nitro-4-hydroxyphenyl)acetic acid (5.65 g.) (syn isomer) with stirring under ice-cooling. The solution was stirred for 30 minutes at room temperature after ether (10 ml.) was added. To the reaction mixture was added petroleum ether under ice-cooling. The precipitates were collected by filtration and thoroughly washed with petroleum ether to give 2-dichloroacetoxyimino-2-(3-nitro-4-hydroxyphenyl)acetic acid (syn isomer) (6.1 g.), which was used as a starting material for the following acylating reaction without further purification.

(4) 2-Hydroxyimino-2-(3-mesylamino-4-hydroxyphenyl)acetic acid (syn isomer) (1.37 g.) and dichloroacetyl chloride (0.9 g.) were treated according to similar manners to those of Preparation 5(1) to 5(3) to give 2-dichloroacetoxyimino-2-(3-mesylamino-4-hydroxyphenyl)acetic acid (syn isomer) (1.9 g.), which was used as a starting material for the following acylating reaction without further purification.

(5) The following compounds were obtained according to similar manners to those of Preparation 5(1) to 5(4).

(1) 2-Dichloroacetoxyimino-2-(4-hydroxyphenyl)acetic acid (syn isomer)

I.R. Spectrum (Nujol) 3350, 1755, 1730 cm$^{-1}$ (2) 2-Dichloroacetoxyimino-2-(3-hydroxyphenyl)acetic acid (a mixture of syn and anti isomers)

I.R. Spectrum (Nujol) 3400, 1760, 1730 cm$^{-1}$ (3) 2-[2-(2-Thienyl)acetoxyimino]-2-(3-hydroxyphenyl)acetic acid (syn isomer)

I.R. Spectrum (Nujol) 3400, 1730–1740 cm$^{-1}$ (4) 2-Benzoyloxyimino-2-(4-hydroxyphenyl)acetic acid (syn isomer)

I.R. Spectrum (Nujol) 3350, 1735, 1725 cm$^{-1}$ (5) 2-Dichloroacetoxyimino-2-(3-methoxy-4-hydroxyphenyl)acetic acid (syn isomer)

I.R. Spectrum (Nujol) 3450, 1795, 1705 cm$^{-1}$ (6) 2-Dichloroacetoxyimino-2-(3-chloro-4-hydroxyphenyl)acetic acid (syn isomer)

I.R. Spectrum (Nujol) 3400, 1780, 1700 cm$^{-1}$ (7) 2-Pivaloyloxyimino-2-(3-hydroxyphenyl)acetic acid (syn isomer), mp 123° to 126° C. (dec.).

EXAMPLE 1

(A) Thionyl chloride (1.3 g.) was added to dimethylformamide (0.8 g.), and the resultant mixture was stirred for 30 minutes at 40° C. The mixture was concentrated to dryness and the residue was dissolved in methylene chloride (15 ml.). 2-Dichloroacetoxyimino-2-(4-hydroxyphenyl)acetic acid (syn isomer) (1.61 g.) was added thereto and the resultant mixture was stirred for 30 minutes at −30° C. To this solution was added at once a solution of 7-amino-3-(1-methyl-1H-tetrazol-5-yl)thiomethyl-3-cephem-4-carboxylic acid (1.64 g.) and bis(trimethylsilyl)acetamide (2.1 g.) in methylene chloride (30 ml.). After stirring for 20 minutes at the same temperature, a small amount of water was added thereto. Methylene chloride was distilled off, and then ethyl acetate and water were added to the residue. After shaking, the ethyl acetate layer was separated (repeated twice). The ethyl acetate layer containing 7-[2-dichloroacetoxyimino-2-(4-hydroxyphenyl)acetamido]-3-(1-methyl-1H-tetrazol-5-yl)thiomethyl-3-cephem-4-carboxylic acid (syn isomer), was washed with a saturated aqueous solution of sodium chloride. Water was added thereto and the resultant mixture was stirred under cooling. A saturated aqueous solution of sodium bicarbonate was added thereto to adjust to pH 7.5. The mixture was stirred for 10 minutes at the same temperature, and then 10% hydrochloric acid was added to the aqueous layer with stirring and cooling to adjust to pH 5. After washing with ethyl acetate, the aqueous layer was further adjusted to pH 2 with 10% hydrochloric acid. After salting-out, it was extracted with ethyl acetate. The extract was washed and dried. The solvent was distilled off. The residue was pulverized with ether, collected by filtration and washed with ether to give 7-[2-hydroxyimino-2-(4-hydroxyphenyl)acetamido]-3-(1-methyl-1H-tetrazol-5-yl)thiomethyl-3-cephem-4-carboxylic acid (syn isomer) (0.46 g.).

I.R. Spectrum (Nujol) 3250, 1770, 1710, 1660 cm$^{-1}$

N.M.R. Spectrum (d$_6$-dimethylsulfoxide, δ): ppm: 11.25 (1H, s); 9.57 (1H, d, J=9 Hz); 7.43 (2H, d, J=9 Hz); 6.80 (2H, d, J=9 Hz); 5.85 (1H, dd, J=5,9 Hz); 5.17 (1H, d, J=5 Hz); 4.32 (2H, AB$_q$, J=13 Hz); 3.95 (3H, s); 3.73 (2H, AB$_q$, J=18 Hz).

Thus obtained 7-[2-hydroxyimino-2-(4-hydroxyphenyl)acetamido]-3-(1-methyl-1H-tetrazol-5-yl)thiomethyl-3-cephem-4-carboxylic acid (syn isomer) was converted by conventional manner into its sodium salt to give sodium 7-[2-hydroxyimino-2-(4-hydroxyphenyl)acetamido]-3-(1-methyl-1H-tetrazol-5-yl)thiomethyl-3-cephem-4-carboxylate (syn isomer).

I.R. Spectrum (Nujol) 3250, 1770, 1710, 1660 cm$^{-1}$

N.M.R. Spectrum (D$_2$O, δ): ppm: 7.5 (2H, d, J=9 Hz); 6.9 (2H, d, J=9 Hz); 5.85 (1H, d, J=5 Hz); 5.16 (1H, d, J=5 Hz); 4.2 (2H, AB$_q$, J=13 Hz); 3.95 (3H, s); 3.6 (2H, AB$_q$, J=18 Hz).

(B) A mixture of dimethylformamide (1.33 g.) and phosphorus oxychloride (2.55 g.) was warmed at 40° C. for 1 hour. After cooling, methylene chloride (30 ml.) was added thereto and distilled off. To the residue was added ethyl acetate (30 ml.). Then, 2-dichloroacetoxyimino-2-(3-hydroxyphenyl)acetic acid (syn isomer) (5.3 g.) was added thereto with stirring under ice-cooling. The resultant mixture was then stirred for 45 minutes at the same temperature. On the other hand, 7-amino-3-(1-methyl-1H-tetrazol-5-yl)thiomethyl-3-cephem-4-carboxylic acid (4.96 g.) and bis(trimethylsilyl)acetamide (9.21 g.) were dissolved in ethyl acetate (50 ml.) and stirred under cooling, to which was added the above obtained solution at −15°-10° C. After stirring for 1 hour at the same temperature, water was added to the reaction solution. The precipitates were filtered off and ethyl acetate layer in the filtrate was separated. After salting-out the aqueous layer, it was extracted with ethyl acetate. Two ethyl acetate layers were combined. Water was added to the extract containing 7-[2-dichloroacetoxyimino-2-(3-hydroxyphenyl)acetamido]-3-(1-methyl-1H-tetrazol-5-yl)thiomethyl-3-cephem-4-carboxylic acid (syn isomer). Then, an aqueous solution of sodium bicarbonate was added thereto to adjust to pH 6–6.5. After stirring for 30 minutes, the aqueous layer was post-treated in a similar manner as in Example 1(A) to give 7-[2-hydroxyimino-2-(3-hydroxyphenyl)acetamido]-3-(1-methyl-1H-tetrazol-5-yl)thiomethyl-3-cephem-4-carboxylic acid (syn isomer) (5.12 g.).

I.R. Spectrum (Nujol) 3300, 1780, 1720, 1670 cm$^{-1}$

N.M.R. Spectrum (d$_6$-dimethylsulfoxide, δ): ppm: 11.6 (1H, s); 9.6 (1H, d, J=9 Hz); 6.7–7.5 (4H, m); 5.85 (1H, dd, J=5,9 Hz); 5.17 (1H, d, J=5 Hz); 4.36 (2H, AB$_q$, J=13 Hz); 3.96 (3H, s); 3.77 (2H, AB$_q$, J=18 Hz).

Thus obtained 7-[2-hydroxyimino-2-(3-hydroxyphenyl)acetamido]-3-(1-methyl-1H-tetrazol-5-yl)thiomethyl-3-cephem-4-carboxylic acid (syn isomer) was converted into its sodium salt by conventional manner to give sodium 7-[2-hydroxyimino-2-(3-hydroxyphenyl)acetamido]-3-(1-methyl-1H-tetrazol-5-yl)thiomethyl-3-cephem-4-carboxylate (syn isomer).

I.R. Spectrum (Nujol) 3200–3500, 1760, 1660, 1595 cm$^{-1}$

N.M.R. Spectrum (D$_2$O, δ): ppm: 6.7–7.5 (4H, m); 5.75 (1H, d, J=5 Hz); 5.1 (1H, d, J=5 Hz); 4.1 (2H, AB$_q$, J=13 Hz); 3.91 (3H, s); 3.55 (2H, AB$_q$, J=18 Hz).

(C) Phosphorus oxychloride (1.77 g.) was added to dry dimethylformamide (0.8 g.) and the mixture was stirred for 30 minutes at 40° C. Dry benzene (20 ml.) was added thereto and the mixture was concentrated to dryness. After the residue was suspended in dry ethyl acetate (20 ml.), to the suspension was dropwise added with cooling at −20° C. and stirring a solution of 2-dichloroacetoxyimino-2-(3-chloro-4-hydroxyphenyl)acetic acid (syn isomer) (3.26 g.) in cooled dry ethyl acetate (20 ml.) and the mixture was stirred for 30 minutes at the same temperature. On the other hand, bis(trimethylsilyl)acetamide (8 g.) was added to a mixture of 7-aminocephalosporanic acid (2.7 g.) and dry ethyl acetate (30 ml.) and the resultant mixture was stirred for 1 hour at ambient temperature. To the resultant solution was dropwise added with stirring and cooling at −20° C. the above obtained ethyl acetate solution and the mixture was stirred for 30 minutes at the same temperature. Water (10 ml.) was dropwise added at −30° C. by small portions to the reaction mixture. Ethyl acetate (100 ml.) and water (80 ml.) were added thereto and the mixture was stirred for 30 minutes. The ethyl acetate layer was separated. To the ethyl acetate solution containing 7-[2-dichloroacetoxyimino-2-(3-chloro-4-hydroxyphenyl)acetamido]cephalosporanic acid (syn isomer) was added water (100 ml.). Sodium bicarbonate was added thereto with ice cooling to adjust the mixture to pH 6.5 and the resultant mixture was stirred for 15 minutes. The aqueous layer was post-treated according to a similar manner to that of Example 1(A) to give 7-[2-hydroxyimino-2-(3-chloro-4-hydroxyphenyl)acetamido]cephalosporanic acid (syn isomer). This compound was suspended in water (20 ml.) and the suspension was adjusted to pH 6.5 by adding sodium bicarbonate and filtered. The filtrate was lyophilized at ambient temperature to give sodium 7-[2-hydroxyimino-2-(3-chloro-4-hydroxyphenyl)acetamido]cephalosporanate (syn isomer) (1.4 g.).

I.R. Spectrum (Nujol) 3400–3450, 3200, 1765, 1720, 1660, 1620, 1660 cm$^{-1}$

N.M.R. Spectrum (D$_2$O, δ): ppm: 7.6 (1H, d, J=2 Hz); 7.3 (1H, dd, J=2,8 Hz); 6.85 (1H, d, J=8 Hz); 5.85 (1H, d, J=6 Hz); 5.20 (1H, d, J=6 Hz); 2.1 (3H, s).

(D) Dimethylformamide (0.4 g.), phosphorus oxychloride (0.81 g.), methylene chloride (20 ml.), ethyl acetate (10 ml.) and 2-[2-(2-thienyl)acetoxyimino]-2-(3-hydroxyphenyl)acetic acid (syn isomer) (1.68 g.) were treated in a manner as in example 1(B) to give an ethyl acetate solution. On the other hand, 7-amino-3-(1-methyl-1H-tetrazol-5-yl)thiomethyl-3-cephem-4-carboxylic acid (1.64 g.) and bis(trimethylsilyl)acetamide (3.55 g.) were dissolved in ethyl acetate (20 ml.) and stirred at −20° C., to which was added the above obtained solution. Then the reaction mixture was stirred for 1 hour at the same temperature. Water was added thereto and the mixture was stirred for 10 minutes. The ethyl acetate layer was separated. The aqueous layer was extracted with ethyl acetate. Two ethyl acetate layers were combined. The extract was washed with a saturated aqueous solution of sodium chloride and dried. The solvent was distilled off. The residue was pulverized with a mixed solution of diisopropylether and ether, collected by filtration and washed to give 7-[2-(2-(2-thienyl)acetoxyimino)-2-(3-hydroxyphenyl)acetamido]-3-(1methyl-1H-tetrazol-5-yl)thiomethyl-3-cephem-4-carboxylic acid (syn isomer) (2.2 g.).

I.R. Spectrum (Nujol) 3150–3200, 1770, 1720, 1670 cm$^{-1}$

N.M.R. Spectrum (d$_6$-dimethylsulfoxide, δ): ppm: 10.12 (1H, d, J=9 Hz); 6.8–7.6 (7H, m); 5.94 (1H, dd, J=5,9 Hz); 5.26 (1H, d, J=5 Hz); 4.38 (2H, AB$_q$, J=13 Hz); 4.18 (2H, s); 3.97 (3H, s); 3.81 (2H, AB$_q$, J=18 Hz).

(E) Dimethylformamide (0.31 g.) and phosphorus oxychloride (0.69 g.) were warmed for 30 minutes at 40° C. To the mixture was added benzene and removed. The residue was suspended in ethyl acetate (7 ml.) and to the suspension was dropwise added, with stirring and cooling at −10° to −20° C., 2-dichloroacetoxyimino-2-(3-hydroxyphenyl)acetic acid (syn isomer) (1.24 g.) in cooled ethyl acetate (6 ml.). The resultant mixture was stirred for 30 minutes at the same temperature. On the other hand, a solution of 7-amino-3-trichloroacetylcarbamoyloxymethyl-3-cephem-4-carboxylic acid (1.05 g.) and bis(trimethylsilyl)acetamide (2.04 g.) in ethyl acetate (10 ml.) was stirred and cooled at −10° to −20° C. To the solution was dropwis added over 5 minutes the above obtained ethyl acetate solution and the mixture was stirred for 2 hours at the same temperature. Water (10 ml.) was added to the reaction mixture and ethyl acetate layer was separated. To the ethyl acetate solution containing 7-[2-dichloroacetoxyimino-2-(3-hydroxyphenyl)acetamido]-3-trichloroacetylcarbamoyloxymethyl-3-cephem-4-carboxylic acid (syn isomer) was added water (10 ml.). The mixture was adjusted to pH 7.5 by adding sodium bicarbonate and stirred for 30 minutes at ambient temperature. The aqueous layer was post-treated according to a similar manner to that of Example 1(A) to give 7-[2-hydroxyimino-2-(3-hydroxyphenyl)acetamido]-3-carbamoyloxymethyl-3-cephem-4-carboxylic acid (syn isomer) (600 mg.). This acid was converted into its sodium salt according to a similar manner to that of Example 1(C) to give sodium 7-[2-hydroxyimino-2-(3-hydroxyphenyl)acetamido]-3-carbamoyloxymethyl-3-cephem-4-carboxylate (syn isomer) (500 mg.).

I.R. Spectrum (Nujol) 3200–3500, 1765, 1660, 1595 cm$^{-1}$

N.M.R. Spectrum (D$_2$O, δ): ppm: 7.0–7.25 (4H, m); 5.85 (1H, d, J=5 Hz); 5.20 (1H, d, J=5 Hz); 4.7 (2H, AB$_q$, J=20 Hz); 3.52 (2H, AB$_q$, J=17 Hz).

(F) 2-Pivaloyloxyimino-2-(3-hydroxyphenyl)acetic acid (syn isomer) (4 g.) and 7-aminocephalosporanic acid (4.08 g.) were treated according to a similar manner to that of Example 1(D) to give powder of 7-[2-pivaloyloxyimino-2-(3-hydroxyphenyl)acetamido]-cephalosporanic acid (syn isomer). This acid was converted into its sodium salt according to a similar manner to that of Example 1(C) to give powder of sodium 7-[2-pivaloyloxyimino-2-(3-hydroxyphenyl)acetamido]-cephalosporanate (syn isomer) (3.8 g.).

(G) The following compounds were obtained according to similar manners to those of Examples 1(A) to 1(F).

(1)  7-[2-Hydroxyimino-2-(3-hydroxyphenyl)acetamido]-3-(1-methyl-1H-tetrazol-5-yl)thiomethyl-3-cephem-4-carboxylic acid (a mixture of syn and anti-isomers)

I.R. Spectrum (Nujol) 3250, 1770, 1710, 1670 cm$^{-1}$

N.M.R. Spectrum (d$_6$-dimethylsulfoxide, δ): ppm: 12.0 (1H, s); 11.5 (1H, s); 9.6 (1H, d, J=9 Hz); 9.0 (1H, d, J=9 Hz); 7.0 (8H, m); 5.8 (2H, m); 5.15 (2H, m); 4.3 (4H, AB$_q$, J=13 Hz); 3.92 (6H, s); 3.7 (4H, AB$_q$, J=18 Hz);

(2)  7-[2-Hydroxyimino-2-(4-hydroxyphenyl)acetamido]-3-(5-methyl-1,3,4-thiadiazol-2-yl)thiomethyl-3-cephem-4-carboxylic acid (syn isomer)

I.R. Spectrum (Nujol) 3250, 1770, 1710, 1660 cm$^{-1}$

N.M.R. Spectrum (d$_6$-dimethylsulfoxide, δ): ppm: 11.17 (1H, s); 9.5 (1H, d, J=9 Hz); 7.35 (2H, d, J=8 Hz); 6.75 (2H, d, J=8 Hz); 5.8 (1H, dd, J=5,9 Hz); 5.15 (1H, d, J=5 Hz); 4.35 (2H, AB$_q$, J=13 Hz); 3.68 (2H, AB$_q$, J—18 Hz); 2.67 (3H, s).

(3)  7-[2-Hydroxyimino-2-(4-hydroxyphenyl)acetamido]-3-(1,3,4-thiadiazol-2-yl)thiomethyl-3-cephem-4-carboxylic acid (syn isomer)

I.R. Spectrum (Nujol) 3250, 1770, 1710, 1660 cm$^{-1}$

N.M.R. Spectrum (d$_6$-dimethylsulfoxide, δ): ppm: 11.13 (1H, s); 9.5 (1H, d, J=9 Hz); 9.41 (1H, s); 7.3 (2H, d, J=9 Hz); 6.7 (2H, d, J=9 Hz); 5.72 (1H, dd, J=5,9 Hz); 5.12 (1H, d, J=5 Hz); 4.38 (2H, AB$_q$, J=13 Hz); 3.65 (2H, AB$_q$, J—18 Hz).

(4)  7-[2-Hydroxyimino-2-(4-hydroxyphenyl)acetamido]-3-(1H-tetrazol-5-yl)thiomethyl-3-cephem-4-carboxylic acid (syn isomer)

I.R. Spectrum (Nujol) 3200, 1770, 1710, 1660 cm$^{-1}$

N.M.R. Spectrum (d$_6$-dimethylsulfoxide, δ): ppm: 11.25 (1H, s); 9.5 (1H, d, J=9 Hz); 7.38 (2H, d, J=8 Hz); 6.8 (2H, d, J=8 Hz); 5.81 (1H, dd, J=5,9 Hz); 5.15 (1H, d, J=5 Hz); 4.30 (2H, AB$_q$, J=13 Hz); 3.68 (2H, AB$_q$, J=18 Hz).

(5)  7-[2-Hydroxyimino-2-(3-hydroxyphenyl)acetamido]-3-(5-methyl-1,3,4-thiadiazol-2-yl)thiomethyl-3-cephem-4-carboxylic acid (syn isomer)

I.R. Spectrum (Nujol) 3270, 1770, 1720, 1660 cm$^{-1}$

N.M.R. Spectrum (d$_6$-dimethylsulfoxide, δ): ppm: 11.68 (1H, s); 9.65 (1H, d, J=9 Hz); 6.7–7.5 (4H, m); 5.85 (1H, dd, J=5,9 Hz); 5.23 (1H, d, J=5 Hz); 4.4 (2H, AB$_q$, J=13 Hz); 3.75 (2H, AB$_q$, J=18 Hz); 2.75 (3H, s).

(6)  7-[2-Hydroxyimino-2-(3-hydroxyphenyl)acetamido]-3-(1,3,4-thiadiazol-2-yl)thiomethyl-3-cephem-4-carboxylic acid (syn isomer)

I.R. Spectrum (Nujol) 3200, 1770, 1710, 1660 cm$^{-1}$

N.M.R. Spectrum (d$_6$-dimethylsulfoxide, δ): ppm: 11.5 (1H, broad s); 9.57 (1H, d, J=9 Hz); 9.5 (1H, s); 6.7–7.45 (4H, m); 5.85 (1H, dd, J=5,9 Hz); 5.16 (1H, d, J=5 Hz); 4.42 (2H, AB$_q$, J=13 Hz); 3.7 (2H, AB$_q$, J=18 Hz).

(7)  7-[2-Benzoyloxyimino-2-(4-hydroxyphenyl)acetamido]-3-(1-methyl-1H-tetrazol-5-yl)thiomethyl-3-cephem-4-carboxylic acid (syn isomer)

I.R. Spectrum (Nujol) 3300, 1785, 1740, 1720, 1670 cm$^{-1}$

N.M.R. Spectrum (d$_6$-dimethylsulfoxide, δ): ppm: 10.15 (1H, d, J=9 Hz); 8.05 (2H, d, J=8 Hz); 7.65 (5H, m); 6.95 (2H, d, J=8 Hz); 6.03 (1H, dd, J=5,9 Hz); 5.23 (1H, d, J=5 Hz); 4.35 (2H, AB$_q$, J=13 Hz); 3.95 (3H, s); 3.75 (2H, AB$_q$, J=18 Hz).

(8) Sodium 7-[2-hydroxyimino-2-(3-methoxy-4-hydroxyphenyl)-acetamido]-3-(1-methyl-1H-tetrazol-5-yl)thiomethyl-3-cephem-4-carboxylate (syn isomer)

I.R. Spectrum (Nujol) 3200–3400, 1770, 1660, 1590 cm$^{-1}$

N.M.R. Spectrum (D₂O, δ): ppm: 6.6–7.3 (3H, m); 5.8 (1H, d, J=5 Hz); 5.15 (1H, d, J=5 Hz); 4.15 (2H, AB$_q$, J=13 Hz); 3.93 (3H, s); 3.82 (3H, s); 3.53 (2H, AB$_q$, J=18 Hz).

(9) 7-[2-Hydroxyimino-2-(3-nitro-4-hydroxyphenyl)acetamido]-3-(1-methyl-1H-tetrazol-5-yl)thiomethyl-3-cephem-4-carboxylic acid (syn isomer)

I.R. Spectrum (Nujol) 3300–3400, 2300–2500, 1770–1780, 1720, 1665, 1620, 1540, 1320 cm⁻¹

N.M.R. Spectrum (D₂O+N$_a$HCO₃, δ): ppm: 7.96 (1H, d, J=2 Hz); 7.50 (1H, dd, J=2,10 Hz); 6.66 (1H, d, J=9 Hz); 5.79 (1H, d, J=4 Hz); 5.15 (1H, d, J=5 Hz); 4.15 (2H, AB$_q$, J=12 Hz); 3.97 (3H, s); 3.60 (2H, AB$_q$, J=12 Hz).

(10) 7-[2-Hydroxyimino-2-(3-chloro-4-hydroxyphenyl)acetamido]-3-(1-methyl-1H-tetrazol-5-yl)thiomethyl-3-cephem-4-carboxylic acid (syn isomer)

I.R. Spectrum (Nujol) 3200–3400, 1780, 1710, 1665 cm⁻¹

N.M.R. Spectrum (d₆-dimethylsulfoxide, δ): ppm: 11.45 (1H, s); 9.65 (1H, d, J=9 Hz); 7.45 (1H, s); 7.4 (1H, dd, J=2,9 Hz); 7.0 (1H, dd, J=2,9 Hz); 5.85 (1H, dd, J=5,9 Hz); 5.20 (1H, d, J=5 Hz); 4.32 (2H, AB$_q$, J=14 Hz); 4.00 (3H, s); 3.75 (2H, AB$_q$, J=18 Hz).

(11) Sodium 7-[2-hydroxyimino-2-(3-mesylamino-4-hydroxyphenyl)acetamido]-3-(1-methyl-1H-tetrazol-5-yl)thiomethyl-3-cephem-4-carboxylate (syn isomer)

I.R. Spectrum (KBr) 3600, 3400, 3200–3300, 1920–1930, 1770, 1660, 1620, 1350, 1150 cm⁻¹

N.M.R. Spectrum (D₂O, δ): ppm: 7.5 (1H, d, J=2 Hz); 6.84 (1H, dd, J=2,8 Hz); 6.60 (1H, d, J=8 Hz); 5.70 (1H, d, J=6 Hz); 5.00 (1H, d, J=6 Hz); 4.3 (2H, d, J=6 Hz); 2.25 (3H, s).

(12) 7-[2-Benzoyloxyimino-2-(3-hydroxyphenyl)acetamido]-3-(1-methyl-1H-tetrazol-5-yl)thiomethyl-3-cephem-4-carboxylic acid (syn isomer)

I.R. Spectrum (Nujol) 3200–3400, 1780, 1720–1760, 1670 cm⁻¹

N.M.R. Spectrum (d₆-dimethylsulfoxide, δ): ppm: 10.12 (1H, d, J=9 Hz); 8.03 (2H, d, J=8 Hz); 6.9–7.8 (6H, m); 6.0 (1H, dd, J=5,9 Hz); 5.22 (1H, d, J=5 Hz); 4.3 (2H, AB$_q$, J=13 Hz); 3.9 (3H, s); 3.71 (2H, AB$_q$, J=18 Hz).

(13) 7-[2-Pivaloyloxyimino-2-(3-hydroxyphenyl)acetamido]-3-(1-methyl-1H-tetrazol-5-yl)thiomethyl-3-cephem-4-carboxylic acid (syn isomer)

I.R. Spectrum (Nujol) 3200–3300, 1760–1780, 1670 cm⁻¹

N.M.R. Spectrum (d₆-dimethylsulfoxide, δ): ppm: 10.0 (1H, d, J=9 Hz); 6.9–7.4 (4H, m); 5.9 (1H, dd, J=5,9 Hz); 5.18 (1H, d, J=5 Hz); 4.31 (2H, AB$_q$, J=13 Hz); 3.95 (3H, s); 3.75 (2H, AB$_q$, J=18 Hz).

(14) 7-[2-Ethoxycarbonyloxyimino-2-(3-hydroxyphenyl)acetamido]-3-(1-methyl-1H-tetrazol-5-yl)thiomethyl-3-cephem-4-carboxylic acid (syn isomer)

I.R. Spectrum (Nujol) 3200–3350, 1775, 1730, 1680 cm⁻¹

N.M.R. Spectrum (d₆-dimethylsulfoxide, δ): ppm: 10.16 (1H, d, J=8 Hz); 7.30–7.70 (4H, m); 5.90 (1H, dd, J=5,8 Hz); 5.21 (1H, d, J=5 Hz); 4.04–4.58 (4H, m); 3.92 (3H, s); 3.74 (2H, AB$_q$, J=17 Hz); 1.30 (3H, t, J=7 Hz).

(15) 7-[2-Acetoxyimino-2-(3-hydroxyphenyl)acetamido]-3-(1-methyl-1H-tetrazol-5-yl)thiomethyl-3-cephem-4-carboxylic acid (syn isomer)

I.R. Spectrum (Nujol) 3250–3450, 1760–1780, 1720, 1670 cm⁻¹

N.M.R. Spectrum (d₆-dimethylsulfoxide, δ): ppm: 10.0 (1H, d, J=9 Hz); 6.9–7.75 (4H, m); 5.92 (1H, dd, J=5,9 Hz); 5.25 (1H, d, J=5 Hz); 4.32 (2H, AB$_q$, J=13 Hz); 3.95 (3H, s); 3.79 (2H, AB$_q$, J=18 Hz); 2.25 (3H, s).

(16) 7-[2-Hydroxyimino-2-(3-nitro-4-hydroxyphenyl)acetamido]-3-carbamoyloxymethyl-3-cephem-4-carboxylic acid (syn isomer)

I.R. Spectrum (Nujol) 3450, 3350, 3250, 2400–2600, 1770, 1725, 1655, 1620, 1535, 1375 cm⁻¹

N.M.R. Spectrum (d₆-dimethylsulfoxide, δ): ppm: 11.72 (1H, s); 9.63 (1H, d, J=8 Hz); 7.96 (1H, d, J=2 Hz); 7.74 (1H, dd, J=2,8 Hz); 7.24 (1H, d, J=8 Hz); 6.57 (2H, s); 5.82 (1H, dd, J=5,8 Hz); 5.20 (1H, d, J=5 Hz); 4.74 (2H, AB$_q$, J=13 Hz); 3.52 (2H, AB$_q$, J=18 Hz).

(17) 7-[2-Hydroxyimino-2-(3-chloro-4-hydroxyphenyl)acetamido]-3-carbamoyloxymethyl-3-cephem-4-carboxylic acid (syn isomer)

I.R. Spectrum (Nujol) 3450, 3250–3350, 1770, 1705, 1660, 1595 cm⁻¹

N.M.R. Spectrum (d₆-dimethylsulfoxide, δ): ppm: 11.56 (1H, s); 9.60 (1H, d, J=8 Hz); 7.46 (1H, d, J=2 Hz); 7.36 (1H, dd, J=2,8 Hz); 7.00 (1H, d, J=8 Hz); 6.59 (2H, s); 5.80 (1H, dd, J=5,8 Hz); 5.18 (1H, d, J=5 Hz); 4.73 (2H, AB$_q$, J=15 Hz); 3.54 (2H, AB$_q$, J=18 Hz).

(18) Pivaloyloxymethyl 7-[2-hydroxyimino-2-(3-hydroxyphenyl)acetamido]-3-(1-methyl-1H-tetrazol-5-yl)thiomethyl-3-cephem-4-carboxylate (syn isomer)

I.R. Spectrum (Nujol) 3300, 1780, 1750, 1660 cm⁻¹

N.M.R. Spectrum (d₆-dimethylsulfoxide, δ): ppm: 11.28 (1H, s); 9.60 (1H, d, J=8 Hz); 6.64–7.36 (4H, m); 5.60–6.0 (3H, m); 5.18 (1H, d, J=5 Hz); 4.30 (2H, AB$_q$, J=13 Hz); 3.94 (3H, s); 3.74 (2H, AB$_q$, J=17 Hz); 1.16 (9H, s).

(19) 7-[2-Hydroxyimino-2-(4-hydroxyphenyl)acetamido]cephalosporanic acid (syn isomer)

I.R. Spectrum (Nujol) 3250, 1770, 1715, 1655 cm⁻¹

N.M.R. Spectrum (d₆-dimethylsulfoxide, δ): ppm: 11.76 (1H, s); 10.10 (1H, d, J=9 Hz); 7.33 (2H, d, J=9 Hz); 6.71 (2H, d, J=9 Hz); 5.80 (1H, dd, J=5,9 Hz); 5.13 (1H, d, J=5 Hz); 4.80 (2H, AB$_q$, J=13 Hz); 3.54 (2H, broad d); 2.00 (3H, s).

(20) 7-[2-Hydroxyimino-2-(3-hydroxyphenyl)acetamido]cephalosphoranic acid (syn isomer)

I.R. Spectrum (Nujol) 3460, 3200, 1780, 1720, 1650 cm⁻¹

N.M.R. Spectrum (d₆-dimethylsulfoxide, δ): ppm: 11.65 (1H, s); 9.6 (1H, d, J=9 Hz); 6.7–7.4 (4H, m); 5.85 (1H, dd, J=5,9 Hz); 5.18 (1H, d, J=5 Hz); 4.87 (2H, AB$_q$, J=13 Hz); 3.57 (2H, AB$_q$, J=18 Hz); 2.0 (3H, s).

(21) Sodium 7-[2-hydroxyimino-2-(3-hydroxyphenyl)acetamido]cephalosporanate (syn isomer)

I.R. Spectrum (Nujol) 3200, 1760, 1720, 1650, 1585 cm⁻¹

N.M.R. Spectrum (D₂O, δ): ppm: 7.45–6.92 (4H, m); 5.85 (1H, d, J=5 Hz); 5.18 (1H, d, J=5 Hz); 4.77 (2H, AB$_q$, J=11 Hz); 3.49 (2H, AB$_q$, J=17 Hz); 2.12 (3H, s).

(22) 7-[2-Hydroxyimino-2-(3-nitro-4-hydroxyphenyl)acetamido]cephalosporanic acid (syn isomer), mp 131° to 133° C. (dec.).

I.R. Spectrum (Nujol) 3300, 3200, 2300–2500, 1770, 1720, 1710, 1650, 1620, 1535, 1320 cm⁻¹

N.M.R. Spectrum (d₆-dimethylsulfoxide, δ): ppm: 11.78 (1H, s); 9.70 (1H, d, J=8 Hz); 8.00 (1H, d, J=2 Hz); 7.78 (1H, dd, J=2,8 Hz); 7.23 (1H, d, J=8 Hz); 5.90 (1H, dd, J=4,6 Hz); 5.22 (1H, d, J=6 Hz); 4.90

(2H, AB$_q$, J=13 Hz); 3.60 (2H, AB$_q$, J=18 Hz); 2.02 (3H, s).

(23) Sodium 7-[2-hydroxyimino-2-(3-mesylamino-4-hydroxyphenyl)acetamido]cephalosporanate (syn isomer)

I.R. Spectrum (Nujol) 3600, 3300–3400, 3200, 1765, 1720, 1660, 1600, 1320, 1150 cm$^{-1}$ N.M.R. Spectrum (D$_2$O, δ): ppm: 7.60 (1H, d, J=2 Hz); 7.40 (1H, dd, J=2,8 Hz); 7.00 (1H, d, J=8 Hz); 5.88 (1H, d, J=6 Hz); 5.20 (1H, d, J=6 Hz); 4.7 (2H, AB$_q$, J=13 Hz); 3.57 (2H, AB$_q$, J=18 Hz); 3.10 (3H, s); 2.10 (3H, s).

(24) Acetoxymethyl 7-[2-hydroxyimino-2-(3-hydroxyphenyl)acetamido]cephalosporanate (syn isomer)

I.R. Spectrum (Nujol) 3300, 1720, 1780, 1660 cm$^{-1}$

N.M.R. Spectrum (d$_6$-dimethylsulfoxide, δ): ppm: 11.52 (1H, s); 9.55 (1H, d, J=8 Hz); 6.7–7.3 (4H, m); 5.7–5.97 (3H, m); 5.19 (1H, d, J=5 Hz); 4.78 (2H, AB$_q$, J=13 Hz); 3.62 (2H, AB$_q$, J=18 Hz); 2.11 (3H, s); 2.08 (3H, s).

(25) Pivaloyloxymethyl 7-[2-hydroxyimino-2-(3-hydroxyphenyl)acetamido]cephalosporanate (syn isomer)

I.R. Spectrum (Nujol) 3300, 1780, 1745, 1660 cm$^{-1}$

N.M.R. Spectrum (d$_6$-dimethylsulfoxide, δ): ppm: 11.26 (1H, s); 9.60 (1H, d, J=8 Hz); 6.60–7.40 (4H, m); 5.65–6.00 (3H, m); 5.20 (1H, d, J=5 Hz); 4.76 (2H, AB$_q$, J=13 Hz); 3.65 (2H, broad s); 2.05 (3H, s); 1.16 (9H, s).

(26) Pivaloyloxymethyl 7-[2-pivaloyloxyimino-2-(3-hydroxyphenyl)acetamido]cephalosporanate (syn isomer)

I.R. Spectrum (Nujol) 3300, 1790, 1750, 1670 cm$^{-1}$

N.M.R. Spectrum (d$_6$-acetone, δ): ppm: 8.9 (1H, d, J=9 Hz); 6.9–7.42 (4H, m); 5.7–7.2 (3H, m); 5.3 (1H, d, J=5 Hz); 4.9 (2H, AB$_q$, J=14 Hz); 3.69 (2H, AB$_q$, J=20 Hz); 2.03 (3H, s); 1.3 (9H, s); 1.21 (9H, s).

EXAMPLE 2

(A) A mixed solution of 7-[2-hydroxyimino-2-(4-hydroxyphenyl)acetamido]cephalosporanic acid (syn isomer) (0.35 g.), 1-methyl-1H-tetrazole-5-thiol (92 mg.), sodium bicarbonate (203 mg.), acetone (5 ml.) and water (10 ml.) was stirred for 6 hours at 60° to 65° C. keeping the pH value around 7. After the reaction solution was washed twice with ethyl acetate, the aqueous layer was adjusted to pH 4.0 by 10% hydrochloric acid and washed twice with ether. Then the pH value of the aqueous layer was charged to 2.5 and it was extracted twice with ethyl acetate. The extract was washed with a saturated aqueous solution of sodium chloride and dried over magnesium sulfate. Thereafter, the solvent was distilled off and the residue, amorphous substance (0.2 g.), was pulverized with ether, collected by filtration and dried to give 7-[2-hydroxyimino-2-(4-hydroxyphenyl)acetamido]-3-(1-methyl-1H-tetrazol-5-yl)thiomethyl-3-cephem-4-carboxylic acid (syn isomer) (90 mg.), pale yellow powder, mp 152° C. (dec).

I.R. Spectrum (Nujol) 3250, 1770, 1710, 1660 cm$^{-1}$

N.M.R. Spectrum (d$_6$-dimethylsulfoxide, δ): ppm: 11.25 (1H, s); 9.57 (1H, d, J=9 Hz); 7.43 (2H, d, J=9 Hz); 6.80 (2H, d, J=9 Hz); 5.85 (1H, dd, J=5,9 Hz); 5.17 (1H, d, J=5 Hz); 4.32 (2H, AB$_q$, J=13 Hz); 3.95 (3H, s); 3.73 (2H, AB$_q$, J=18 Hz).

Thus obtained 7-[2-hydroxyimino-2-(4-hydroxyphenyl)acetamido]-3-(1-methyl-1H-tetrazol-5-yl)thiomethyl-3-cephem-4-carboxylic acid (syn isomer) was converted by conventional manner into its sodium salt to give sodium 7-[2-hydroxyimino-2-(4-hydroxyphenyl)acetamido]-3-(1-methyl-1H-tetrazol-5-yl)thiomethyl-3-cephem-4-carboxylate (syn isomer).

I.R. Spectrum (Nujol) 3250, 1770, 1710, 1660 cm$^{-1}$

N.M.R. Spectrum (D$_2$O, δ): ppm: 7.5 (2H, d, J=9 Hz); 6.9 (2H, d, J=9 Hz); 5.85 (1H, d, J=5 Hz); 5.16 (1H, d, J=5 Hz); 4.2 (2H, AB$_q$, J=13 Hz); 3.95 (3H, s); 3.6 (2H, AB$_q$, J=18 Hz).

(B) The following compounds were obtained according to a similar manner to that of Example 2(A).

(1) 7-[2-Hydroxyimino-2-(3-hydroxyphenyl)acetamido]-3-(1-methyl-1H-tetrazol-5-yl)thiomethyl-3-cephem-4-carboxylic acid (syn isomer).

I.R. Spectrum (Nujol) 3300, 1780, 1720, 1670 cm$^{-1}$

N.M.R. Spectrum (d$_6$-dimethylsulfoxide, δ): ppm: 11.6 (1H, s); 9.6 (1H, d, J=9 Hz); 6.7–7.5 (4H, m); 5.85 (1H, dd, J=5,9 Hz); 5.17 (1H, d, J=5 Hz); 4.36 (2H, AB$_q$, J=13 Hz); 3.96 (3H, s); 3.77 (2H, AB$_q$, J=18 Hz).

(2) Sodium 7-[2-hydroxyimino-2-(3-hydroxyphenyl)acetamido]-3-(1-methyl-1H-tetrazol-5-yl)thiomethyl-3-cephem-4-carboxylate (syn isomer)

I.R. Spectrum (Nujol) 3200–3500, 1760, 1660, 1595 cm$^{-1}$

N.M.R. Spectrum (D$_2$O, δ): ppm: 6.7–7.5 (4H, m); 5.75 (1H, d, J=5 Hz); 5.1 (1H, d, J=5 Hz); 4.1 (2H, AB$_q$, J=13 Hz); 3.91 (3H, s); 3.55 (2H, AB$_q$, J=18 Hz).

(3) 7-[2-Hydroxyimino-2-(3-hydroxyphenyl)acetamido]-3-(1-methyl-1H-tetrazol-5-yl)thiomethyl-3-cephem-4-carboxylic acid (a mixture of syn and anti-isomers)

I.R. Spectrum (Nujol) 3250, 1770, 1710, 1670 cm$^{-1}$

N.M.R. Spectrum (d$_6$-dimethylsulfoxide, δ): ppm: 12.0 (1H, s); 11.5 (1H, s); 9.6 (1H, d, J=9 Hz); 9.0 (1H, d, J=9 Hz); 7.0 (8H, m); 5.8 (2H, m); 5.15 (2H, m); 4.3 (4H, AB$_q$, J=13 Hz); 3.92 (6H, s); 3.7 (4H, AB$_q$, J=18 Hz).

(4) 7-[2-Hydroxyimino-2-(4-hydroxyphenyl)acetamido]-3-(5-methyl-1,3,4-thiadiazol-2-yl)thiomethyl-3-cephem-4-carboxylic acid (syn isomer)

I.R. Spectrum (Nujol) 3250, 1770, 1710, 1660 cm$^{-1}$

N.M.R. Spectrum (d$_6$-dimethylsulfoxide, δ): ppm: 11.17 (1H, s); 9.5 (1H, d, J=9 Hz); 7.35 (2H, d, J=8 Hz); 6.75 (2H, d, J=8 Hz); 5.8 (1H, dd, J=5,9 Hz); 5.15 (1H, d, J=5 Hz); 4.35 (2H, AB$_q$, J=13 Hz); 3.68 (2H, AB$_q$, J=18 Hz); 2.67 (3H, s).

(5) 7-[2-Hydroxyimino-2-(4-hydroxyphenyl)acetamido]-3-(1,3,4-thiadiazol-2-yl)thiomethyl-3-cephem-4-carboxylic acid (syn isomer)

I.R. Spectrum (Nujol) 3250, 1770, 1710, 1660 cm$^{-1}$

N.M.R. Spectrum (d$_6$-dimethylsulfoxide, δ): ppm: 11.13 (1H, s); 9.5 (1H, d, J=9 Hz); 9.41 (1H, s); 7.3 (2H, d, J=9 Hz); 6.7 (2H, d, J=9 Hz); 5.72 (1H, dd, J=5,9 Hz); 5.12 (1H, d, J=5 Hz); 4.38 (2H, AB$_q$, J=13 Hz); 3.65 (2H, AB$_q$, J=18 Hz).

(6) 7-[2-Hydroxyimino-2-(4-hydroxyphenyl)acetamido]-3-(1H-tetrazol-5-yl)thiomethyl-3-cephem-4-carboxylic acid (syn isomer)

I.R. Spectrum (Nujol) 3200, 1770, 1710, 1660 cm$^{-1}$

N.M.R. Spectrum (d$_6$-dimethylsulfoxide, δ): ppm: 11.25 (1H, s); 9.5 (1H, d, J=9 Hz); 7.38 (2H, d, J=8 Hz); 6.8 (2H, d, J=8 Hz); 5.81 (1H, dd, J=5,9 Hz); 5.15 (1H, d, J=5 Hz); 4.30 (2H, AB$_q$, J=13 Hz); 3.68 (2H, AB$_q$, J=18 Hz).

(7) 7-[2-Hydroxyimino-2-(3-hydroxyphenyl)acetamido]-3-(5-methyl-1,3,4-thiadiazol-2-yl)thiomethyl-3-cephem-4-carboxylic acid (syn isomer)

I.R. Spectrum (Nujol) 3270, 1770, 1720, 1660 cm$^{-1}$

N.M.R. Spectrum (d$_6$-dimethylsulfoxide, δ): ppm: 11.68 (1H, s); 9.65 (1H, d, J=9 Hz); 6.7–7.5 (4H, m);

5.85 (1H, dd, J=5.9 Hz); 5.23 (1H, d, J=5 Hz); 4.4 (2H, AB$_q$, J=13 Hz); 3.75 (2H, AB$_q$, J=18 Hz); 2.75 (3H, s).

(8) 7-[2-Hydroxyimino-2-(3-hydroxyphenyl)acetamido]-3-(1,3,4-thiadiazol-2-yl)thiomethyl-3-cephem-4-carboxylic acid (syn isomer)

I.R. Spectrum (Nujol) 3200, 1770, 1710, 1660 cm$^{-1}$

N.M.R. Spectrum (d$_6$-dimethylsulfoxide, δ): ppm: 11.5 (1H, broad s); 9.57 (1H, d, J=9 Hz); 9.5 (1H, s); 6.7–7.45 (4H, m); 5.85 (1H, dd, J=5,9 Hz); 5.16 (1H, d, J=5 Hz); 4.42 (2H, AB$_q$, J=13 Hz); 3.7 (2H, AB$_q$, J=18 Hz).

(9) 7-[2-Benzoyloxyimino-2-(4-hydroxyphenyl)acetamido]-3-(1-methyl-1H-tetrazol-5-yl)thiomethyl-3-cephem-4-carboxylic acid (syn isomer)

I.R. Spectrum (Nujol) 3300, 1785, 1740, 1720, 1670 cm$^{-1}$

N.M.R. Spectrum (d$_6$-dimethylsulfoxide), δ): ppm: 10.15 (1H, d, J=9 Hz); 8.05 (2H, d, J=8 Hz); 7.65 (5H, m); 6.95 (2H, d, J=8 Hz); 6.03 (1H, dd, J=5,9 Hz); 5.23 (1H, d, J=5 Hz); 4.35 (2H, AB$_q$, J=13 Hz); 3.95 (3H, s); 3.75 (2H, AB$_q$, J=18 Hz).

(10) Sodium 7-[2-hydroxyimino-2-(3-methoxy-4-hydroxyphenyl)acetamido]-3-(1-methyl-1H-tetrazol-5-yl)thiomethyl-3-cephem-4-carboxylate (syn isomer)

I.R. Spectrum (Nujol) 3200–3400, 1770, 1660, 1590 cm$^{-1}$

N.M.R. Spectrum (D$_2$O, δ): ppm: 6.6–7.3 (3H, m); 5.8 (1H, d, J=5 Hz); 5.15 (1H, d, J=5 Hz); 4.15 (2H, AB$_q$, J=13 Hz); 3.93 (3H, s); 3.82 (3H, s); 3.53 (2H, AB$_q$, J=18 Hz).

(11) 7-[2-Hydroxyimino-2-(3-nitro-4-hydroxyphenyl)acetamido]-3-(1-methyl-1H-tetrazol-5-yl)thiomethyl-3-cephem-4-carboxylic acid (syn isomer)

I.R. Spectrum (Nujol) 3300–3400, 2300–2500, 1770–1780, 1720, 1665, 1620, 1540, 1320 cm$^{-1}$ N.M.R. Spectrum (D$_2$O+N$_a$HCO$_3$, δ): ppm: 7.96 (1H, d, J=2 Hz); 7.50 (1H, dd, J=2,10 Hz); 6.66 (1H, d, J=9 Hz); 5.79 (1H, d, J=4 Hz); 5.15 (1H, d, J=5 Hz); 4.15 (2H, AB$_q$, J=12 Hz); 3.97 (3H, s); 3.60 (2H, AB$_q$, J=12 Hz).

(12) 7-[2-Hydroxyimino-2-(3-chloro-4-hydroxyphenyl)acetamido]-3-(1-methyl-1H-tetrazol-5-yl)thiomethyl-3-cephem-4-carboxylic acid (syn isomer)

I.R. Spectrum (Nujol) 3200–3400, 1780, 1710, 1665 cm$^{-1}$

N.M.R. Spectrum (d$_6$-dimethylsulfoxide, δ): ppm: 11.45 (1H, s); 9.65 (1H, d, J=9 Hz); 7.45 (1H, s); 7.4 (1H, dd, J=2,9 Hz); 7.0 (1H, dd, J=2,9 Hz); 5.85 (1H, dd, J=5,9 Hz); 5.20 (1H, d, J=5 Hz); 4.32 (2H, AB$_q$, J=14 Hz); 4.00 (3H, s); 3.75 (2H, AB$_q$, J=18 Hz).

(13) Sodium 7-[2-hydroxyimino-2-(3-mesylamino-4-hydroxyphenyl)acetamido]-3-(1-methyl-1H-tetrazol-5-yl)thiomethyl-3-cephem-4-carboxylate (syn isomer)

I.R. Spectrum (KB$_r$) 3600, 3400, 3200–3300, 1920–1930, 1770, 1660, 1620, 1350, 1150 cm$^{-1}$ N.M.R. Spectrum (D$_2$O, δ): ppm: 7.5 (1H, d, J=2 Hz); 6.84 (1H, dd, J=2,8 Hz); 6.60 (1H, d, J=8 Hz); 5.70 (1H, d, J=6 Hz); 5.00 (1H, d, J=6 Hz); 4.3 (2H, d, J=6 Hz); 2.25 (3H, s).

(14) 7-[2-Benzoyloxyimino-2-(3-hydroxyphenyl)acetamido]-3-(1-methyl-1H-tetrazol-5-yl)thiomethyl-3-cephem-4-carboxylic acid (syn isomer)

I.R. Spectrum (Nujol) 3200–3400, 1780, 1720–1760, 1670 cm$^{-1}$

N.M.R. Spectrum (d$_6$-dimethylsulfoxide, δ): ppm: 10.12 (1H, d, J=9 Hz); 8.03 (2H, d, J=8 Hz); 6.9–7.8 (6H, m); 6.0 (1H, dd, J=5,9 Hz); 5.22 (1H, d, J=5 Hz); 4.3 (2H, AB$_q$, J=13 Hz); 3.9 (3H, s); 3.71 (2H, AB$_q$, J=18 Hz).

(15) 7-[2-Pivaloyloxyimino-2-(3-hydroxyphenyl)acetamido]-3-(1-methyl-1H-tetrazol-5-yl)thiomethyl-3-cephem-4-carboxylic acid (syn isomer)

I.R. Spectrum (Nujol) 3200–3300, 1760–1780, 1670 cm$^{-1}$

N.M.R. Spectrum (d$_6$-dimethylsulfoxide, δ): ppm: 10.0 (1H, d, J=9 Hz); 6.9–7.4 (4H, m); 5.9 (1H, dd, J=5,9 Hz); 5.18 (1H, d, J=5 Hz); 4.31 (2H, AB$_q$, J=13 Hz); 3.95 (3H, s); 3.75 (2H, AB$_q$, J=18 Hz).

(16) 7-[2-Acetoxyimino-2-(3-hydroxyphenyl)acetamido]-3-(1-methyl-1H-tetrazol-5-yl)thiomethyl-3-cephem-4-carboxylic acid (syn isomer)

I.R. Spectrum (Nujol) 3250–3450, 1760–1780, 1720, 1670 cm$^{-1}$

N.M.R. Spectrum (d$_6$-dimethylsulfoxide, δ): ppm: 10.0 (1H, d, J=9 Hz); 6.9–7.75 (4H, m); 5.92 (1H, dd, J=5,9 Hz); 5.25 (1H, d, J=5 Hz); 4.32 (2H, AB$_q$, J=13 Hz); 3.95 (3H, s); 3.79 (2H, AB$_q$, J=18 Hz); 2.25 (3H, s).

(17) Pivaloyloxymethyl 7-[2-hydroxyimino-2-(3-hydroxyphenyl)acetamido]-3-(1-methyl-1H-tetrazol-5-yl)thiomethyl-3-cephem-4-carboxylate (syn isomer)

I.R. Spectrum (Nujol) 3300, 1780, 1750, 1660 cm$^{-1}$

N.M.R. Spectrum (d$_6$-dimethylsulfoxide, δ): ppm: 11.28 (1H, s); 9.60 (1H, d, J=8 Hz); 6.64–7.36 (4H, m); 5.60–6.0 (3H, m); 5.18 (1H, d, J=5 Hz); 4.30 (2H, AB$_q$, J=13 Hz); 3.94 (3H, s); 3.74 (2H, AB$_q$, J=17 Hz); 1.16 (9H, s).

EXAMPLE 3

(A) Ethyl chloroformate (10.9 g.) was dropwise added by small portions with stirring and ice-cooling to a solution of sodium 7-[2-hydroxyimino-2-(3-hydroxyphenyl)acetamido]-3-(1-methyl-1H-tetrazol-5-yl)thiomethyl-3-cephem-4-carboxylate (syn isomer) (16.3 g.) in a mixture of water (80 ml.) and pyridine (80 ml.), and the mixture was stirred for 1 hour at the same temperature. Water (200 ml.) was added thereto and the mixture was washed with ether. The aqueous layer was adjusted to pH 2 with hydrochloric acid and extracted with ethyl acetate. The extract was washed with dilute hydrochloric acid and with a sodium chloride aqueous solution and dried over magnesium sulfate. After treating with activated charcoal, the solvent was distilled off and the residual oil was pulverized with a mixture of diisopropyl ether and ether. The powder was collected by filtration, dried and suspended in water (150 ml.). To the suspension was added sodium bicarbonate (1.7 g.). The solution was adjusted to pH 6 with dilute hydrochloric acid and treated with activated charcoal. Dilute hydrochloric acid was added thereto with cooling and stirring and precipitates were collected by filtration, washed with water and dried to give 7-[2-ethoxycarbonyloxyimino-2-(3-hydroxyphenyl)acetamido]-3-(1-methyl-1H-tetrazol-5-yl)thiomethyl-3-cephem-4-carboxylic acid (syn isomer) (9.4 g.).

I.R. Spectrum (Nujol) 3200–3350, 1775, 1730, 1680 cm$^{-1}$

N.M.R. Spectrum (d$_6$-dimethylsulfoxide, δ): ppm: 10.16 (1H, d, J=8 Hz); 7.30–7.70 (4H, m); 5.90 (1H, dd, J=5, 8 Hz); 5.21 (1H, d, J=5 Hz); 4.04–4.58 (4H, m); 3.92 (3H, s); 3.74 (2H, AB$_q$, J=17 Hz); 1.30 (3H, t, J=7 Hz).

(B) A mixture of 7-[2-hydroxyimino-2-(3-hydroxyphenyl)acetamido]-3-(1-methyl-1H-tetrazol-5-yl)thiomethyl-3-cephem-4-carboxylic acid (syn isomer) (9.83 g.) and acetic anhydride (200 ml.) was stirred for 5 hours at ambient temperature. The reaction mixture was concentrated under reduced pressure. To the residue was added ether and the mixture was stirred overnight at ambient temperature. Precipitates were collected by filtration, washed thoroughly with ether and dried to give 7-[2-acetoxyimino-2-(3-hydroxyphenyl)acetamido]-3-(1-methyl-1H-tetrazol-5-yl)thiomethyl-3-cephem-4-carboxylic acid (syn isomer) (8.5 g.).

I.R. Spectrum (Nujol) 3250–3450, 1760–1780, 1720, 1670 cm$^{-1}$

N.M.R. Spectrum (d$_6$-dimethylsulfoxide, δ): ppm: 10.0 (1H, d, J=9 Hz); 6.9–7.75 (4H, m); 5.92 (1H, dd, J=5,9 Hz); 5.25 (1H, d, J=5 Hz); 4.32 (2H, AB$_q$, J=13 Hz); 3.95 (3H, s); 3.79 (2H, AB$_q$, J=18 Hz); 2.25 (3H, s).

(C) The following compounds were obtained according to similar manners to those of Examples 3(A) to 3(B).

(1) 7-[2-{2-(2-Thienyl)acetoxyimino}-2-(3-hydroxyphenyl)acetamido]-3-(1-methyl-1H-tetrazol-5-yl)thiomethyl-3-cephem-4-carboxylic acid (syn isomer)

I.R. Spectrum (Nujol) 3150–3200, 1770, 1720, 1670 cm$^{-1}$

N.M.R. Spectrum (d$_6$-dimethylsulfoxide, δ): ppm: 10.12 (1H, d, J=9 Hz); 6.8–7.6 (7H, m); 5.94 (1H, dd, J=5,9 Hz); 5.26 (1H, d, J=5 Hz); 4.38 (2H, AB$_q$, J=13 Hz); 4.18 (2H, s); 3.97 (3H, s); 3.81 (2H, AB$_q$, J=18 Hz).

(2) 7-[2-Benzoyloxyimino-2-(4-hydroxyphenyl)acetamido]-3-(1-methyl-1H-tetrazol-5-yl)thiomethyl-3-cephem-4-carboxylic acid (syn isomer)

I.R. Spectrum (Nujol) 3300, 1785, 1740, 1720, 1670 cm$^{-1}$

N.M.R. Spectrum (d$_6$-dimethylsulfoxide, δ): ppm: 10.15 (1H, d, J=9 Hz); 8.05 (2H, d, J=8 Hz); 7.65 (5H, m); 6.95 (2H, d, J=8 Hz); 6.03 (1H, dd, J=5,9 Hz); 5.23 (1H, d, J=5 Hz); 4.35 (2H, AB$_q$, J=13 Hz); 3.95 (3H, s); 3.75 (2H, AB$_q$, J=18 Hz).

(3) 7-[2-Benzoyloxyimino-2-(3-hydroxyphenyl)acetamido]-3-(1-methyl-1H-tetrazol-5-yl)thiomethyl-3-cephem-4-carboxylic acid (syn isomer)

I.R. Spectrum (Nujol) 3200–3400, 1780, 1720–1760, 1670 cm$^{-1}$

N.M.R. Spectrum (d$_6$-dimethylsulfoxide, δ): ppm: 10.12 (1H, d, J=9 Hz); 8.03 (2H, d, J=8 Hz); 6.9–7.8 (6H, m); 6.0 (1H, dd, J=5,9 Hz); 5.22 (1H, d, J=5 Hz); 4.3 (2H, AB$_q$, J=13 Hz); 3.9 (3H, s); 3.71 (2H, AB$_q$, J=18 Hz).

(4) 7-[2-Pivaloyloxyimino-2-(3-hydroxyphenyl)acetamido]-3-(1-methyl-1H-tetrazol-5-yl)thiomethyl-3-cephem-4-carboxylic acid (syn isomer)

I.R. Spectrum (Nujol) 3200–3300, 1760–1780, 1670 cm$^{-1}$

N.M.R. Spectrum (d$_6$-dimethylsulfoxide, δ): ppm: 10.0 (1H, d, J=9 Hz); 6.9–7.4 (4H, m); 5.9 (1H, dd, J=5,9 Hz); 5.18 (1H, d, J=5 Hz); 4.31 (2H, AB$_q$, J=13 Hz); 3.95 (3H, s); 3.75 (2H, AB$_q$, J=18 Hz).

(5) Pivaloyloxymethyl 7-[2-pivaloyloxyimino-2-(3-hydroxyphenyl)acetamido]cephalosporanate (syn isomer)

I.R. Spectrum (Nujol) 3300, 1790, 1750, 1670 cm$^{-1}$

N.M.R. Spectrum (d$_6$-acetone, δ): ppm: 8.9 (1H, d, J=9 Hz); 6.9–7.42 (4H, m); 5.7–7.2 (3H, m); 5.3 (1H, d, J=5 Hz); 4.9 (2H, AB$_q$, J=14 Hz); 3.69 (2H, AB$_q$, J=20 Hz); 2.03 (3H, s); 1.3 (9H, s); 1.21 (9H, s).

(6) 7-[2-Pivaloyloxyimino-2-(3-hydroxyphenyl)acetamido]cephalosporaic acid (syn isomer), powder, and its sodium salt (syn isomer), powder.

EXAMPLE 4

(A) A solution of iodomethyl acetate (0.87 g.) in dimethylformamide (4 ml.) was added at once with stirring and ice-cooling to a solution of sodium 7-[2-hydroxyimino-2-(3-hydroxyphenyl)acetamido]cephalosporanate (syn isomer) (2 g.) in dimethylformamide (20 ml.), and the mixture was stirred for 20 minutes at the same temperature. Ethyl acetate (100 ml.) was added thereto and then the ethyl acetate solution was in turn washed with water (80 ml.) (3 times), with a 5% sodium bicarbonate aqueous solution (40 ml.) (twice) and with a sodium chloride aqueous solution (80 ml.) (twice). The ethyl acetate solution was dried, treated with activated charcoal and concentrated. To the residue was added diisopropyl ether and the mixtures was stirred overnight at ambient temperature. Precipitates were collected by filtration, washed with diisopropyl ether and dried to give acetoxymethyl 7-[2-hydroxyimino-2-(3-hydroxyphenyl)acetamido]cephalosporanate (syn isomer) (1.4 g.).

I.R. Spectrum (Nujol) 3300, 1720–1780, 1660 cm$^{-1}$

N.M.R. Spectrum (d$_6$-dimethylsulfoxide, δ): ppm: 11.52 (1H, s); 9.55 (1H, d, J=8 Hz); 6.7–7.3 (4H, m); 5.7–5.97 (3H, m); 5.19 (1H, d, J=5 Hz); 4.78 (2H, AB$_q$, J=13 Hz); 3.62 (2H, AB$_q$, J=18 Hz); 2.11 (3H, s); 2.08 (3H, s).

(B) The following compounds were obtained according to a similar manner to that of Example 4(A).

(1) Pivaloyloxymethyl 7-[2-hydroxyimino-2-(3-hydroxyphenyl)acetamido]-3-(1-methyl-1H-tetrazol-5-yl)thiomethyl-3-cephem-4-carboxylate (syn isomer)

I.R. Spectrum (Nujol) 3300, 1780, 1750, 1660 cm$^{-1}$

N.M.R. Spectrum (d$_6$-dimethylsulfoxide, δ): ppm: 11.28 (1H, s); 9.60 (1H, d, J=8 Hz); 6.64–7.36 (4H, m); 5.60–6.0 (3H, m); 5.18 (1H, d, J=5 Hz); 4.30 (2H, AB$_q$, J=13 Hz); 3.94 (3H, s); 3.74 (2H, AB$_q$, J=17 Hz); 1.16 (9H, s).

(2) Pivaloyloxymethyl 7-[2-hydroxyimino-2-(3-hydroxyphenyl)acetamido]cephalosporanate (syn isomer)

I.R. Spectrum (Nujol) 3300, 1780, 1745, 1660 cm$^{-1}$

N.M.R. Spectrum (d$_6$-dimethylsulfoxide, δ): ppm: 11.26 (1H, s); 9.60 (1H, d, J=8 Hz); 6.60–7.40 (4H, m); 5.65–6.00 (3H, m); 5.20 (1H, d, J=5 Hz); 4.76 (2H, AB$_q$, J=13 Hz); 3.65 (2H, broad s); 2.05 (3H, s); 1.16 (9H, s).

(3) Pivaloyloxymethyl 7-[2-pivaloyloxyimino-2-(3-hydroxyphenyl)acetamido]cephalosporanate (syn isomer)

I.R. Spectrum (Nujol) 3300, 1790, 1750, 1670 cm$^{-1}$

N.M.R. Spectrum (d$_6$-acetone, δ): ppm: 8.9 (1H, d, J=9 Hz); 6.9–7.42 (4H, m); 5.7–7.2 (3H, m); 5.3 (1H, d, J=5 Hz); 4.9 (2H, AB$_q$, J=14 Hz); 3.69 (2H, AB$_q$, J=20 Hz); 2.03 (3H, s); 1.3 (9H, s); 1.21 (9H, s).

What we claim is:

1. 7-(α,α-Disubstituted-acetamido)-3-substituted-3-cephem-4-carboxylic acid (syn isomer) of the formula:

wherein $R^1$ is hydrogen, halogen or nitro, and pharmaceutically acceptable salts thereof.

2. The compounds of claim 1, wherein $R^1$ is hydrogen.

3. The compound of claim 2, which is 7-[2-hydroxyimino-2-(3-hydroxyphenyl)acetamido]-3-carbamoyloxymethyl-3-cephem-4-carboxylic acid and its sodium salt.

4. The compounds of claim 1, wherein $R^1$ is halogen.

5. The compounds of claim 4, wherein $R^1$ is chlorine.

6. The compound of claim 5, which is 7-[2-hydroxyimino-2-(3-chloro-4-hydroxypheny)acetamido]-3-carbamoyloxymethyl-3-cephem-4-carboxylic acid.

7. The compounds of claim 1, wherein $R^1$ is nitro.

8. The compound of claim 7, which is 7-[2-hydroxyimino-2-(3-nitro-4-hydroxyphenyl)acetamido]-3-carbamoyloxymethyl-3-cephem-4-carboxylic acid.

9. An antibacterial composition comprising an antibacterially effective amount of a compound of claim 1 in association with a pharmaceutically acceptable, substantially non-toxic carrier or excipient.

* * * * *